United States Patent
Yates

(10) Patent No.: US 8,114,592 B2
(45) Date of Patent: Feb. 14, 2012

(54) GENETIC MARKERS ASSOCIATED WITH AGE-RELATED MACULAR DEGENERATION, METHODS OF DETECTION AND USES THEREOF

(75) Inventor: John R. W. Yates, Cambridge (GB)

(73) Assignee: Cambridge Enterprise Limited, Cambridge (GB)

( * ) Notice: Subject to any disclaimer, the term of this patent is extended or adjusted under 35 U.S.C. 154(b) by 239 days.

(21) Appl. No.: 12/382,569

(22) Filed: Mar. 18, 2009

(65) Prior Publication Data

US 2009/0269761 A1 Oct. 29, 2009

Related U.S. Application Data

(60) Provisional application No. 61/037,411, filed on Mar. 18, 2008.

(51) Int. Cl.
*C12Q 1/68* (2006.01)
*C12P 19/34* (2006.01)
*C07H 21/02* (2006.01)
*C07H 21/04* (2006.01)

(52) U.S. Cl. ....... 435/6.1; 435/91.2; 536/23.1; 536/24.3

(58) Field of Classification Search .............. None
See application file for complete search history.

(56) References Cited

U.S. PATENT DOCUMENTS

2009/0111708 A1 * 4/2009 Seddon et al. ............... 506/9

FOREIGN PATENT DOCUMENTS

| CA | 2 363 503 | 9/2000 |
|---|---|---|
| CA | 2 407 715 | 11/2001 |
| WO | WO 2006/062716 | 6/2006 |

OTHER PUBLICATIONS

Hegele, R.A. Arterioscler Thromb Vasc Biol (2002), vol. 22, pp. 1058-1061.*
Juppner H. Bone (Aug. 1995) vol. 17, No. 2, Supplement, pp. 39S-42S.*
Pennisi E. Science (Sep. 18, 1998) vol. 281, No. 5384, pp. 1787-1789.*
Wall, J.D. et al. Nature Reviews—Genetics (Aug. 2003) vol. 4 pp. 587-597.*
Yates et al, "Complement C3 Variant and the Risk of Age-Related Macular Degeneration", The New England Journal of Medicine 357:553-561 (2007).
Maller et al, "Variation in complement factor 3 is associated with risk of age-related macular degeneration", Nature Genetics 39(10):1200-1201 (2007).

* cited by examiner

*Primary Examiner* — Stephen Kapushoc
(74) *Attorney, Agent, or Firm* — Nixon & Vanderhye P.C.

(57) ABSTRACT

Disclosed is a method for identifying an individual who has an altered risk for developing age related macular degeneration comprising detecting a single nucleotide polymorphism (SNP).

2 Claims, No Drawings

GENETIC MARKERS ASSOCIATED WITH AGE-RELATED MACULAR DEGENERATION, METHODS OF DETECTION AND USES THEREOF

CROSS-REFERENCE PARAGRAPH

This application claims the benefit of U.S. Provisional Application No. 61/037,411 filed on Mar. 18, 2008, the entire content of which is incorporated herein by reference in its entirety.

TECHNICAL FIELD OF THE INVENTION

This invention is related to the area of genetic testing, drug discovery, and Age-Related Macular Degeneration. In particular, it relates to genetic variants found within the complement cascade C3 gene which increase the risk of Age-Related Macular Degeneration.

BACKGROUND OF THE INVENTION

Age-related macular degeneration (AMD) causes progressive impairment of central vision and is the leading cause of irreversible vision loss in older Americans(1). The most severe form of AMD involves neovascular/exudative (wet) and/or atrophic (dry) changes to the macula. Although the etiology of AMD remains largely unknown, implicated risk factors include age, ethnicity, smoking, hypertension, obesity and diet (2). Familial aggregation (3), twin studies (4), and segregation analysis(5) suggest that there is also a significant genetic contribution to the disease. The candidate gene approach and genome-wide association studies have consistently implicated the CFH, ARMS2 and C2/BF genes, all members of the complement-mediated inflammatory cascade.

Age-related macular degeneration (AMD) is a common complex disorder that affects the central region of the retina (macula) and is the leading cause of legal blindness in older American adults. The prevalence of AMD and its significant morbidity will rise sharply as the population ages. AMD is a clinically heterogeneous disorder with a poorly understood etiology. Population-based longitudinal studies(6-8) have established that the presence of extracellular protein/lipid deposits (drusen) between the basal lamina of the retinal pigment epithelium (RPE) and the inner layer of Bruchs' membrane is associated with an increased risk of progressing to an advanced form of AMD, either geographic atrophy or exudative disease. The presence of large and indistinct (soft) drusen coupled with RPE abnormalities is considered an early form of the disorder and is often referred to as age-related maculopathy (ARM).

Epidemiology: AMD is a complex disorder with contributions of environmental factors as well as genetic susceptibility(2). Many environmental and lifestyle factors have been postulated, but by far the most consistently implicated non-genetic risk factor for AMD is cigarette smoking (6). Much progress has been made in identifying and characterizing the genetic basis of AMD. In a remarkable example of the convergence of methods for disease gene discovery, multiple independent research efforts identified the Y402H variant in the complement factor H(CFH [(MIM 134370]) gene on chromosome 1q32 as the first major AMD susceptibility allele (9-14). While one of the studies was able to pinpoint CFH on the basis of a whole-genome association study (11), most studies focused on the 1q32 region because it had consistently been implicated by several whole-genome linkage scans. Disease associated haplotypes within the CFH gene are also associated with AMD (15). A second genomic region with similarly consistent linkage evidence is chromosome 10q26, which was identified as the single most promising region by a recent meta-analysis of published linkage screens (16).

Two studies have suggested specific AMD susceptibility genes located on chromosome 10q26. One used a combination of family-based and case-control analyses to implicate the PLEKHA1 gene (pleckstrin homology domain containing, family A (phosphoinositide binding specific) member 1 [MIM 607772]) and the predicted ARMS2 gene (14;17;18). ARMS2 appears to be a mitochondrial membrane protein involved in inflammation (19) A second study using two independent case-control datasets concluded that the T allele of SNP rs10490924 in ARMS2, a coding change (Ala69Ser) in exon 1 of this gene, was the most likely AMD susceptibility allele (16). Both studies reported that the chromosome 10q26 variant confers an AMD risk similar in magnitude to that of the Y402H variant in CFH. A locus with less strong association, but reproducible association with AMD is the complement component 2 (C2) and Factor B (C2/BF) locus within the major histocompatability complex III locus found on chromosome 6 The L9H variant of BF and the E318D variant of C2, as well as a variant in intron 10 of C2 and the R32Q variant of BF, confer a significantly reduced risk of AMD (20).

SUMMARY OF THE INVENTION

Here, we describe highly significant association of SNPs within the C3 gene (NCBI GeneID: 718), specifically rs2230199 (Arg102Gly) found on chromosome 19 with age related macular degeneration and its use, alone or in combination, in predicting predisposition to this disease (21). We have thus established that identification of the nucleotide residue at rs2230199 can predict the predisposition of an individual to AMD. Related findings have since been published by Maller et al. (22).

According to some embodiments of the invention, a method is provided for assessing increased risk of Age Related Macular Degeneration. The identity is determined of at least one nucleotide residue of the genomic germ-line C3 coding sequence of an individual The nucleotide residue is identified as normal or variant by comparing it to a normal genomic germ-line sequence of C3 coding sequence as shown in SEQ ID NO:1 (coding sequence) or SEQ ID NO: 3 (genomic sequence). A normal nucleotide residue is identical to the corresponding nucleotide residue in the normal genomic germ-line sequence of C3. A variant nucleotide residue is not identical to the corresponding nucleotide residue in the normal genomic germ-line sequence of C3. A variant C3 coding sequence may contain at least one variant nucleotide residue relative to the normal C3 coding sequence. An individual with a variant sequence has a higher risk of Age Related Macular Degeneration than an individual with a normal sequence.

According to some embodiments, a method is provided for assessing increased risk of Age Related Macular Degeneration. The identity is determined of at least one amino acid residue of the C3 protein of an individual. The at least one amino acid residue is identified as normal or variant by comparing it to a normal sequence of the C3 protein as shown in SEQ ID NO: 2. A person with a variant sequence has a higher risk of Age Related Macular Degeneration than a person with a normal sequence.

Further embodiments of the invention provide a method to assess risk of AMD in an individual. The presence of a G or C allele at the single nucleotide polymorphism (SNP)rs 2230199 within the genomic sequence is determined in an individual. The person is identified as being at high risk of AMD if the patient has one or two copies of the G allele on the negative genomic strand at this SNP (or conversely one or two copies of the C allele on the positive genomic strand) in relation to the March 2006 human reference sequence (NCBI Build 36.1). The SNP rs2230199 is found in the first position of codon 102 (corresponding to position 366 in the C3 coding sequence of SEQ ID NO: 1 or 304 nucleotides downstream of the start of the initiation codon). SNP rs2230199 is located at position 6669387 on human chromosome 19 ((NCBI Build 36.1). The G allele changes the amino acid specified from arginine to glycine. The patient is identified as being at lower risk of AMD if the patient does not have one or two copies of the G allele at rs2230199.

Further embodiments provide a method for assessing increased risk of Age Related Macular Degeneration. The identity of the residue at position 102 of the pro-C3 protein sequence or position 80 of the mature C3 protein sequence is determined in an individual. The residue is identified as normal or variant by comparing it to a normal sequence of the pro-C3 protein or C3 protein as shown in SEQ ID NO: 2. An individual with a variant sequence has a higher risk of Age Related Macular Degeneration than an individual with a normal sequence. For example, an individual with Gly at position 102 has a higher risk of Age Related Macular Degeneration than an individual with Arg at position 102.

While not being bound by any theory, this marker, or one in linkage disequilibrium, may change the composition, function or abundance of the elements of cellular constituents resulting in a predisposition to age related macular degeneration. Measuring this marker in individuals who do not ostensibly have age related macular degeneration may identify those at heightened risk for the subsequent development of age related macular degeneration, providing benefit for, but not limited to, individuals, insurers, care givers and employers. Information obtained from the detection of SNPs associated with age related macular degeneration is of great value in the treatment and prevention of this condition.

In the context of this invention, a marker is said to be in "linkage disequilibrium" with the residue at rs2230199 when the correlation coefficient ($r^2$) between the marker and rs2230199 is >0.5 (23).

Further scope of the applicability of the present invention will become apparent from the detailed description provided below. It should be understood however, that the following detailed description and examples, while indicating preferred embodiments of the invention, are given by way of illustration only, since various changes and modification within the spirit and scope of the invention will become apparent to those skilled in the art from the following detailed description.

DETAILED DESCRIPTION OF THE INVENTION

The present inventors have discovered that polymorphic variants in the C3 gene, which is shown in sequences, SEQ ID NOs: 1-3 are associated with an altered risk of developing age related macular degeneration in subjects. The present invention thus provides a SNP associated with age related macular degeneration, nucleic acid molecules containing the SNP, methods and reagents for the detection of the SNP disclosed herein, uses of this SNP for the development of detection reagents, and assays or kits that utilize such reagents. The age related macular degeneration-associated SNP disclosed herein may be useful for diagnosing, screening for, and evaluating predisposition to age related macular degeneration and related pathologies in humans.

The age related macular degeneration-associated SNP has been identified by genotyping DNA from 1548 individuals, 847 of these individuals having been previously diagnosed with age related macular degeneration and 701 being "control" or individuals thought to be free of age related macular degeneration.

Aspects of the present invention thus provides an individual SNP associated with age related macular degeneration, genomic sequences (SEQ ID NO: 3) containing SNPs, transcript sequences (SEQ ID NO: 1) and amino acid sequences (SEQ ID NO: 2). Aspects of the invention include methods of detecting these polymorphisms in a test sample, methods of determining the risk of an individual of having or developing age related macular degeneration, methods of using the disclosed SNPs to select a treatment strategy, and methods of using the SNPs of the present invention for human identification.

When the presence in the genome of an individual of a particular base, e.g., guanine, at a particular location in the genome (e.g. the SNP rs2230199) correlates with an increased probability of that individual contracting age related macular degeneration vis-à-vis a population not having that base at that location in the genome, that individual is said to be at "increased risk" of contracting age related macular degeneration, i.e., to have an increased susceptibility. In the present case, such increased probability exists when the base is present in one or the other or both alleles of the individual. Furthermore, the probability is increased when the base is present in both alleles of the individual rather than one allele of the individual.

When the presence in the genome of an individual of a particular base, e.g., cytosine, at a particular location in the genome (e.g. the SNP rs2230199) decreases the probability of that individual contracting age related macular degeneration vis-à-vis a population not having that base at that location in the genome, that individual is said to be at "decreased risk" of contracting age related macular degeneration, i.e., to have a decreased susceptibility. Such an allele is sometimes referred to in the art as being "protective". As with increased risk, it is also possible for a decreased risk to be characterized as dominant or recessive.

An "altered risk" means either an increased or a decreased risk.

The genetic analysis detailed below linked age related macular degeneration with a SNP in the human genome. A SNP is a particular type of polymorphic site, a polymorphic site being a region in a nucleic acid sequence at which two or more alternative nucleotides are observed in a significant number of individuals from a population. A polymorphic site may be a nucleotide sequence of two or more nucleotides, an inserted nucleotide or nucleotide sequence, a deleted nucleotide or nucleotide sequence, or a microsatellite, for example. A polymorphic site that is two or more nucleotides in length may be 3, 4, 5, 6, 7, 8, 9, 10, 11, 12, 13, 14, 15 or more, 20 or more, 30 or more, 50 or more, 75 or more, 100 or more, 500 or more, or about 1000 nucleotides in length, where all or some of the nucleotide sequences differ within the region. The specific polymorphic site found in the genomic sequences identified as SEQ ID NOs: 1 and 3 is a "single nucleotide polymorphism" or a "SNP" i.e. a polymorphic site which is one nucleotide in length.

Where there are two, three, or four alternative nucleotide sequences at a polymorphic site, each nucleotide sequence is referred to as a "polymorphic variant" or "nucleic acid variant." Where two polymorphic variants exist, for example, the polymorphic variant represented in a majority of samples from a population is sometimes referred to as a "prevalent allele" and the polymorphic variant that is less prevalently represented is sometimes referred to as an "uncommon allele." An individual who possesses two prevalent alleles or two uncommon alleles is "homozygous" with respect to the polymorphism, and an individual who possesses one prevalent allele and one uncommon allele is "heterozygous" with respect to the polymorphism. Individuals who are homozygous with respect to one allele are sometimes predisposed to a different phenotype as compared to individuals who are heterozygous or homozygous with respect to another allele.

A genotype or polymorphic variant may also be expressed in terms of a "haplotype," which refers to the identity of two or more polymorphic variants occurring within genomic DNA on the same strand of DNA. For example, two SNPs may exist within a gene where each SNP position may include a cytosine variation or an adenine variation. Certain individuals in a population may carry an allele (heterozygous) or two alleles (homozygous) having the gene with a cytosine at each SNP position. As the two cytosines corresponding to each SNP in the gene travel together on one or both alleles in these individuals, the individuals can be characterized as having a cytosine/cytosine haplotype with respect to the two SNPs in the gene.

A "phenotype" is a trait which can be compared between individuals, such as presence or absence of a condition, for example, occurrence of age related macular degeneration.

Polymorphic variants are often reported without any determination of whether the variant is represented in a significant fraction of a population. Some reported variants are sequencing errors and/or not biologically relevant. Thus, it is often not known whether a reported polymorphic variant is statistically significant or biologically relevant until the presence of the variant is detected in a population of individuals and the frequency of the variant is determined.

A polymorphic variant may be detected on either or both strands of a double-stranded nucleic acid. Also, a polymorphic variant may be located within an intron or exon of a gene or within a portion of a regulatory region such as a promoter, a 5' untranslated region (UTR), a 3' UTR, and in DNA (e.g., genomic DNA (gDNA) and complementary DNA (cDNA)), RNA (e.g., mRNA, tRNA, and rRNA), or a polypeptide. Polymorphic variations may or may not result in detectable differences in gene expression, polypeptide structure, or polypeptide function.

In our genetic analysis associating age related macular degeneration with the polymorphic variants set forth in Table 1, samples from individuals diagnosed with age related macular degeneration and individuals not having age related macular degeneration were allelotyped and genotyped. The allele frequency for each polymorphic variant among cases and controls was determined. These allele frequencies were compared in cases and controls, or combinations. Particular SNPs were thus found to be associated with age related macular degeneration when genotype and haplotype frequency differences calculated between case and control pools were established to be statistically significant.

As mentioned above, polymorphic variants can travel together. Such variants are said to be in "linkage disequilibrium" so that heritable elements e.g., alleles that have a tendency to be inherited together instead of being inherited independently by random assortment are in linkage disequilibrium. Alleles are randomly assorted or inherited independently of each other if the frequency of the two alleles together is the product of the frequencies of the two alleles individually. For example, if two alleles at different polymorphic sites are present in 50% of the chromosomes in a population, then they would be said to assort randomly if the two alleles are present together on 25% of the chromosomes in the population. A higher percentage would mean that the two alleles are linked. For example, a first polymorphic site P1 having two alleles, e.g. A and C—each appearing in 50% of the individuals in a given population, is said to be in linkage disequilibrium with a second polymorphic site P2 having two alleles e.g. G and T—each appearing in 50% of the individuals in a given population, if particular combinations of alleles are observed in individuals at a frequency greater than 25% (if the polymorphic sites are not linked, then one would expect a 50% chance of an individual having A at P1 and a 50% chance of having G at P2 thus leading to a 25% chance of having the combination of A at P1 and G at P2 together). Heritable elements that are in linkage disequilibrium are said to be "linked" or "genetically linked" to each other.

One can see that in the case of a group of SNPs that are in linkage disequilibrium with each other, knowledge of the existence of all such SNPs in a particular individual generally provides redundant information. Thus, when identifying an individual who has an altered risk for developing age related macular degeneration according to this invention, it is necessary to detect only one SNP of such a group of SNPs associated with an altered risk of developing age related macular degeneration.

The data set out below shows that one or more SNPs in the C3 genomic sequences identified herein as SEQ ID NOs: 1 and 3 are associated with the occurrence of age related macular degeneration. Thus, featured herein are methods for identifying a risk of age related macular degeneration in a subject, which includes detecting the presence or absence of a polymorphic variant at one or more of the SNPs described herein in a human nucleic acid sample. For example, the presence or absence of a polymorphic variant at rs2230199 (e.g. the G allele) may be detected in a human nucleic acid sample.

Three different analyses were performed for each marker and significant results reported below as follows: (a) a test of trend across the 3 genotypes(24), (b) a dominant model where the homozygous genotype for allele "B" is combined with the prevalent heterozygote genotype; and (c) a recessive model where the homozygous genotype for allele "A" is combined with the heterozygous genotype. An empirical p-value for the largest of these three test statistics was calculated by permutations. In addition, a Mantel-Haenszel odds ratio measuring the change in risk associated with each additional copy of allele B is also calculated and reported.

Pertinent results for the SNP are summarized in Table 1: Chromosomal number and position- using the International Human Genome Sequencing Consortium build 35 (http://www.ncbi.nlm.nih.gov/genome/seq/) as made available by the National Center for Biotechnology Information (NCBI), National Library of Medicine, Building 38A, Bethesda, Md. 20894 U.S.A., gene marker name-using the nomenclature of the NCBI dbSNP (URLf[colon][slash][slash]www[dot]ncbi[dot]nlm[dot]nih[dot]gov[slash]SNP[slash]) and gene name-using the unigene naming convention. Under the "Case Flag" the number 1 designates Cases and the number 0 designates Controls. The identity of the base designated "A" in the analysis is indicated where 1=A (adenine), 2=C (cytosine), 3=G (guanine) and 4=T (thymidine). "B" indicates the polymorphic allele. AA, AB, BB are the counts of the number of individuals with the given genotype, by cases/controls. The odds ratio is the Mantel-Haenszel odds ratio across the three genotypes.

It has been discovered that polymorphic variation at SNPs in the C3 genomic sequences which are identified herein as SEQ ID NOs: 1 or 3 is associated with the occurrence of age related macular degeneration. Thus, featured herein are methods for identifying a risk of age related macular degeneration in a subject, which comprises detecting the presence or absence of one or more of the polymorphic variations described herein in a human nucleic acid sample. The polymorphic variations and SNPs are detailed in the table. In some embodiments, the presence of a polymorphic variant at rs2230199 is indicative of an altered risk of age related macular degeneration. For example, the presence of the uncommon G allele at rs2230199 may be indicative of an increased risk of age related macular degeneration, relative to individuals with the prevalent C allele at rs2230199.

Methods for determining whether a subject is at risk of age related macular degeneration are provided herein. These methods include detecting the presence or absence of one or more polymorphic variations at SNPs which are associated with age related macular degeneration, in a sample from a subject.

SNPs may be associated with a disease state such as AMD, in humans or in animals. The association can be direct, as in conditions where the substitution of a base results in alteration of the protein coding sequence of a gene which contributes directly to the pathophysiology of the condition. Common examples of this include diseases such as sickle cell anemia and cystic fibrosis. The association can be indirect when the SNP plays no role in the disease, but is located close to the defective gene such that there is a strong association between the presence of the SNP and the disease state. Because of the high frequency of SNPs within the genome, there is a greater probability that a SNP will be linked to a genetic locus of interest than other types of genetic markers.

Disease-associated SNPs may occur in coding and non-coding regions of the genome. When located in the coding region altered function of the ensuing protein sequence may occur. For example, polymorphic variation at SNP rs2230199 may alter the amino acid residue at position 102 of the C3 pro-protein. If it occurs in the regulatory region of a gene it may affect expression of the protein. If the protein is involved in protecting the body against pathological conditions this can result in disease susceptibility.

Numerous methods exist for the measurement of specific SNP genotypes. Individuals carrying mutations in one or more SNPs of the present invention may be detected at the DNA level by a variety of techniques. Nucleic acids for diagnosis may be obtained from a patient's cells, such as from blood, urine, saliva, tissue biopsy and autopsy material.

The genomic DNA may be used directly for detection or may be amplified enzymatically by using PCR prior to analysis (25). RNA or cDNA may also be used in the same ways. As an example, PCR primers complementary to the nucleic acid of one or more SNPs of the present invention can be used to identify and analyze the presence or absence of the SNP. For example, deletions and insertions can be detected by a change in size of the amplified product in comparison to the normal genotype. Point mutations can be identified by hybridizing amplified DNA to radiolabeled SNP RNA of the present invention or alternatively, radiolabeled SNP antisense DNA sequences of the present invention. Perfectly matched sequences can be distinguished from mismatched duplexes by RNase A digestion or by differences in melting temperatures.

Sequence differences between a reference gene and genes having mutations also may be revealed by direct DNA sequencing. In addition, cloned DNA segments may be employed as probes to detect specific DNA segments. The sensitivity of such methods can be greatly enhanced by appropriate use of PCR or another amplification method. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures(26).

Sequence changes at specific locations also may be revealed by nuclease protection assays, such as RNase and S1 protection or the chemical cleavage method(27).

Thus, the detection of a specific DNA sequence may be achieved by methods which include, but are not limited to, hybridization, RNase protection, chemical cleavage, direct DNA sequencing or the use of restriction enzymes, (e.g., restriction fragment length polymorphisms ("RFLP") and Southern blotting of genomic DNA).

Hybridisation may be carried out under stringent hybridization conditions, for example for detection of sequences that are about 80-90% identical suitable conditions include hybridization overnight at 42° C. in 0.25M $Na_2HPO_4$, pH 7.2, 6.5% SDS, 10% dextran sulfate and a final wash at 55° C. in 0.1×SSC, 0.1% SDS. For detection of sequences that are greater than about 90% identical, suitable conditions include hybridization overnight at 65° C. in 0.25M $Na_2HPO_4$, pH 7.2, 6.5% SDS, 10% dextran sulfate and a final wash at 60° C. in 0.1×SSC, 0.1% SDS.

In addition to more conventional gel-electrophoresis and DNA sequencing, mutations also can be detected by in situ analysis.

Genetic mutations can be identified by hybridizing a sample and control nucleic acids, e.g., DNA or RNA, to high density arrays containing hundreds or thousands of oligonucleotides probes(28;29). For example, genetic mutations can be identified in two-dimensional arrays containing light-generated DNA probes as described in Cronin et al., supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene. Specific mutations can also be determined through direct sequencing of one or both strands of DNA using dideoxy nucleotide chain termination chemistry, electrophoresis through a semi-solid matrix and fluorescent or radioactive chain length detection techniques. Further mutation detection techniques may involve differential susceptibility of the polymorphic double strand to restriction endonuclease digestion, or altered electrophoretic gel mobility of single or double stranded gene fragments containing one polymorphic form. Other techniques to detect specific DNA polymorphisms or mutation may involve evaluation of the structural characteristics at the site of polymorphism using nuclear magnetic resonance or x-ray diffraction techniques.

These genetic tests are useful for prognosing and/or diagnosing age related macular degeneration and often are useful for determining whether an individual is at an increased or decreased risk of developing or having age related macular degeneration.

Thus, the invention includes a method for identifying a subject at risk of age related macular degeneration, which includes detecting in a nucleic acid sample from the subject the presence or absence of a polymorphic variant at a SNP associated with age related macular degeneration in a nucleotide sequence identified as SEQ ID NOs:1 and 3.

For example, the presence of one or two copies of the G allele at SNP rs2230199 may be indicative of the subject being at risk of age related macular degeneration i.e. an individual at risk of AMD may be heterozygous (genotype GC) or homozygous (genotype GG) at SNP rs2230199 in the C3 gene, Results from prognostic tests may be combined with other test results to diagnose age related macular degeneration. For example, prognostic results may be gathered, a patient sample may be ordered based on a determined predisposition to age related macular degeneration, the patient sample analyzed, and the results of the analysis may be utilized to diagnose age related macular degeneration. Also age related macular degeneration diagnostic methods can be developed from studies used to generate prognostic/diagnostic methods in which populations are stratified into subpopulations having different progressions of age related macular degeneration. In some embodiments, prognostic results may be gathered; a patient's risk factors for developing age related macular degeneration analyzed (e.g., age, family history, smoking); and a patient sample may be ordered based on a determined predisposition to age related macular degeneration. In some embodiments, the results from predisposition analyses may be combined with other test results, epidemiologic or genetic in nature, indicative of age related macular degeneration, which were previously, concurrently, or subsequently gathered with respect to the predisposition testing. In these embodiments, the combination of the prognostic test results with other test results can be probative of age related macular degeneration, and the combination can be utilized as a age related macular degeneration diagnostic.

Risk of age related macular degeneration sometimes is expressed as a probability, such as an odds ratio, percentage, or risk factor. The risk is based upon the presence or absence of the SNP variant described herein, and also may be based in part upon phenotypic traits of the individual being tested. Methods for calculating risk based upon patient data are well known (30). Allelotyping and genotyping analyses may be carried out in populations other than those exemplified herein to enhance the predictive power of the prognostic method. These further analyses are executed in view of the exemplified procedures described herein, and may be based upon the same polymorphic variations or additional polymorphic variations. Risk determinations for age related macular degeneration are useful in a variety of applications. In some embodiments, age related macular degeneration risk determinations may be used by clinicians to direct appropriate detection, preventative and treatment procedures to subjects who most require these. In other embodiments, age related macular degeneration risk determinations may be used by health insurers for preparing actuarial tables and for calculating insurance premiums.

The nucleic acid sample typically is isolated from a biological sample obtained from a subject. For example, nucleic acid can be isolated from blood, saliva, sputum, urine, cell scrapings, and biopsy tissue. The nucleic acid sample can be isolated from a biological sample using standard techniques. The nucleic acid sample may be isolated from the subject and then directly utilized in a method for determining the presence of a polymorphic variant, or alternatively, the sample may be isolated and then stored (e.g., frozen) for a period of time before being subjected to analysis.

The presence or absence of a polymorphic variant may be determined using one or both chromosomal complements represented in the nucleic acid sample. Determining the presence or absence of a polymorphic variant in both chromosomal complements represented in a nucleic acid sample is useful for determining the zygosity of an individual for the polymorphic variant (i.e., whether the individual is homozygous or heterozygous for the polymorphic variant). For example, a homozygous individual having the GG genotype at SNP rs2230199 (i.e. the G allele in both copies of the C3 gene) may have an increased risk of AMD relative to a heterozygous individual having the GC genotype at SNP rs2230199 (i.e. the G allele in one copies of the C3 gene and the C allele in the other)

Any oligonucleotide-based diagnostic may be utilized to determine whether a sample includes the presence or absence of a polymorphic variant in a sample. For example, primer extension methods, ligase sequence determination methods (e.g., U.S. Pat. Nos. 5,679,524 and 5,952,174, and WO 01/27326), mismatch sequence determination methods (e.g., U.S. Pat. Nos. 5,851,770; 5,958,692; 6,110,684; and 6,183, 958), microarray sequence determination methods, restriction fragment length polymorphism (RFLP), single strand conformation polymorphism detection (SSCP) (e.g., U.S. Pat. Nos. 5,891,625 and 6,013,499), PCR-based assays (e.g., TAQMAN™ PCR System (Applied Biosystems)), and nucleotide sequencing methods may be used.

Oligonucleotide extension methods typically involve providing a pair of oligonucleotide primers in a polymerase chain reaction (PCR) or in other nucleic acid amplification methods for the purpose of amplifying a region from the nucleic acid sample that comprises the polymorphic variation. One oligonucleotide primer is complementary to a region 3' of the polymorphism and the other is complementary to a region 5' of the polymorphism. A PCR primer pair may be used in methods disclosed in U.S. Pat. Nos. 4,683, 195; 4,683,202, 4,965,188; 5,656,493; 5,998,143; 6,140,054; WO 01/27327; and WO 01/27329 for example. PCR primer pairs may also be used in any commercially available machines that perform PCR, such as any of the GENE-AMP™, systems available from Applied Biosystems. Also, those of ordinary skill in the art will be able to design oligonucleotide primers based upon the nucleotide sequences set forth in SEQ ID NOs: 1 and 3.

Also provided is an extension oligonucleotide that hybridizes to the amplified fragment adjacent to the polymorphic variation. An adjacent fragment refers to the 3' end of the extension oligonucleotide being often 1 nucleotide from the 5' end of the polymorphic site, and sometimes 2, 3, 4, 5, 6, 7, 8, 9, or 10 nucleotides from the 5' end of the polymorphic site, in the nucleic acid when the extension oligonucleotide is hybridized to the nucleic acid. The extension oligonucleotide then is extended by one or more nucleotides, and the number and/or type of nucleotides that are added to the extension oligonucleotide determine whether the polymorphic variant is present. Oligonucleotide extension methods are disclosed, for example, in U.S. Pat. Nos. 4,656,127; 4,851,331; 5,679, 524; 5,834,189; 5,876,934; 5,908,755; 5,912,118; 5,976,802; 5,981,186; 6,004,744; 6,013,431; 6,017,702; 6,046,005; 6,087,095; 6,210,891; and WO 01/20039. Oligonucleotide extension methods using mass spectrometry are described, for example, in U.S. Pat. Nos. 5,547,835; 5,605,798; 5,691,141; 5,849,542; 5,869,242; 5,928,906; 6,043,031; and 6,194,144. Multiple extension oligonucleotides may be utilized in one reaction, which is referred to as multiplexing.

A microarray can be utilized for determining whether a SNP is present or absent in a nucleic acid sample. A microarray may include any oligonucleotides described herein, and methods for making and using oligonucleotide microarrays suitable for diagnostic use are disclosed in U.S. Pat. Nos. 5,492,806; 5,525,464; 5,589,330; 5,695,940; 5,849,483; 6,018,041; 6,045,996; 6,136,541; 6,142,681; 6,156;501; 6,197,506; 6,223,127; 6,225,625; 6,229,911; 6,239,273; WO 00/52625; WO 01/25485; and WO 01/29259. The microarray typically comprises a solid support and the oligonucleotides may be linked to this solid support by covalent bonds or by non-covalent interactions. The oligonucleotides may also be linked to the solid support directly or by a spacer molecule. A microarray may comprise one or more oligonucleotides complementary to a nucleotide sequence which includes a SNP set forth in Table 1. The one or more oligonucleotides may for example, hybridise specifically to a nucleotide sequence which comprises a particular polymorphic variant at the SNP, but not to nucleotide sequences which comprise other polymorphic variants at the SNP. A kit also may be utilized for determining whether a polymorphic variant is present or absent in a nucleic acid sample. A kit may include one or more pairs of oligonucleotide primers useful for amplifying a fragment of a nucleotide sequence of interest, where the fragment includes a polymorphic site. The kit may comprise a polymerizing agent, for example, a thermostable nucleic acid polymerase such as one disclosed in U.S. Pat. No. 4,889,818 or 6,077,664. Also, the kit may comprise an elongation oligonucleotide that hybridizes to the nucleotide sequence in a nucleic acid sample adjacent to the polymorphic site. Where the kit includes an elongation oligonucleotide, it may also comprise chain elongating nucleotides, such as dATP, dTTP, dGTP, dCTP, and dITP, including analogs of dATP, dTTP, dGTP, dCTP and dITP, provided that such analogs are substrates for a thermostable nucleic acid polymerase and can be incorporated into a nucleic acid chain elongated from the extension oligonucleotide. Along with chain elongating nucleotides may be one or more chain terminating nucleotides such as ddATP, ddTTP, ddGTP, ddCTP. The kit may comprise one or more oligonucleotide primer pairs, a polymerizing agent, chain elongating nucleotides, at least one elongation oligonucleotide, and one or more chain terminating nucleotides. Kits optionally include buffers, vials, microtiter plates, and instructions for use.

An individual identified as being susceptible to age related macular degeneration may be heterozygous or homozygous with respect to the allele associated with an increased risk of age related macular degeneration, as indicated in the table. For example, the individual may be heterozygous or homozygous with respect to the G allele of rs2230199 which is shown herein to be associated with an increased risk of age related macular degeneration. A subject homozygous for an allele associated with an increased risk of age related macular degeneration is at a comparatively high risk of age related macular degeneration as far as that SNP is concerned whether or not the allelic effect has been determined to be dominant or recessive. A subject who is heterozygous for an allele associated with an increased risk of age related macular degeneration, in which the allelic effect is recessive would likely be at a comparatively reduced risk of age related macular degeneration predicted by that SNP. The allelic effect of the G allele of rs2230199 is shown herein to be dominant and an individual who is heterozygous for the G allele may be at an increased risk of age related macular degeneration relative to individuals who lack the G allele.

Individuals carrying mutations in one or more SNP of the present invention may be detected at the protein level by a variety of techniques. Cells suitable for diagnosis may be obtained from a patient's blood, urine, saliva, tissue biopsy and autopsy material.

Also featured are methods for determining risk of age related macular degeneration and/or identifying a subject at risk of age related macular degeneration by contacting a polypeptide or protein encoded by a nucleotide sequence from a subject with an antibody that specifically binds to an epitope associated with an altered, usually increased risk of age related macular degeneration in the polypeptide.

Another aspect of the invention provides an isolated nucleic acid molecule comprising at least 8, or at least 9, or at least 10, or at least 11, or at least 12, or at least 13, or at least 14, or at least 15, or at least 16, or at least 17, or at least 18, or at least 19, or at least 20, or at least 21, or at least 22, or at least 23, or at least 24, or at least 25, or at least 26, or at least 27, or at least 28, or at least 29, or at least 30, or at least 31, or at least 32, or at least 33, or at least 34, or at least 35, or at least 36, or at least 37, or at least 38, or at least 39, or at least 40, or at least 41, or at least 42, or at least 43, or at least 44, or at least 45, or at least 46, or at least 47, or at least 48, or at least 49, or at least 50, or at least 51, or at least 52, or at least 53, or at least 54, or at least 55, or at least 56, or at least 57, or at least 58, or at least 59, or at least 60, or at least 61, or at least 62, or at least 63, or at least 64, or at least 65, or at least 66, or at least 67, or at least 68, or at least 69, or at least 70, or at least 71, or at least 72, or at least 73, or at least 74, or at least 75, or at least 76, or at least 77, or at least 78, or at least 79, or at least 80, or at least 81, or at least 82, or at least 83, or at least 84, or at least 85, or at least 86, or at least 87, or at least 88, or at least 89, or at least 90, or at least 91, or at least 92, or at least 93, or at least 94, or at least 95, or at least 96, or at least 97, or at least 98, or at least 99, or at least 100 contiguous nucleotides from any one of SEQ NOS: 1 or 3 wherein one of the nucleotides is located at the site of single nucleotide polymorphism (SNP) corresponding to single nucleotide polymorphism (SNP) at rs2230199 on human chromosome 19 as set out herein or the complement thereof, and optionally, wherein the isolated nucleic acid molecule has a maximum length of 100 said contiguous nucleotides, or a maximum length of 90 said contiguous nucleotides, or a maximum length of 80 said contiguous nucleotides, or a maximum length of 70 said contiguous nucleotides, or a maximum length of 60 said contiguous nucleotides, or a maximum length of 50 said contiguous nucleotides, or a maximum length of 40 said contiguous nucleotides, or a maximum length of 30 said contiguous nucleotides, or a maximum length of 20 said contiguous nucleotides.

Oligonucleotides can be linked to a second moiety, which can be another nucleic acid molecule to provide, for example, a tail sequence (e.g., a polyadenosine tail), an adapter sequence (e.g., phage M13 universal tail sequence), etc. Alternatively, the moiety might be one that facilitates linkage to a solid support or a detectable label, e.g., a radioactive label, a fluorescent label, a chemiluminescent label, a paramagnetic label, etc.

Nucleic acid sequences shown in SEQ ID NO: 1, 3 or 4, or fragments thereof, may be used for diagnostic purposes for detection of polypeptide expression.

DNA encoding a polypeptide can also be used in the diagnosis of age related macular degeneration. For example, the nucleic acid sequence can be used in hybridization assays of biopsies or autopsies to polymorphic variants associated with increased risk of AMD (e.g., Southern or Northern blot analysis, in situ hybridization assays).

Expression of a polypeptide during embryonic development can also be determined using nucleic acid encoding the polypeptide, particularly production of a functionally impaired polypeptide that is the cause of age related macular degeneration. In situ hybridizations using a polypeptide as a probe can be employed to predict problems related to age related macular degeneration.

Included as part of this invention are nucleic acid vectors, often expression vectors, which contain a nucleotide sequence set forth in the SEQ ID NO:1 or 3, or a fragment thereof. A vector is a nucleic acid molecule capable of transporting another nucleic acid to which it has been linked and can include a plasmid, cosmid, or viral vector. The vector can be capable of autonomous replication or it can integrate into a host DNA. Viral vectors may include replication defective retroviruses, adenoviruses and adeno-associated viruses for example.

A vector can include a nucleotide sequence from SEQ ID NO: 1 or 3 or a fragment thereof, in a form suitable for expression of an encoded protein or nucleic acid in a host cell. The recombinant expression vector generally includes one or more regulatory sequences operatively linked to the nucleic acid sequence to be expressed. A regulatory sequence includes promoters, enhancers and other expression control elements (e.g., polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of expression of polypeptide desired, etc. Expression vectors can be introduced into host cells to produce the desired polypeptides, including fusion polypeptides.

Recombinant expression vectors can be designed for expression of polypeptides in prokaryotic or eukaryotic cells. For example, the polypeptides can be expressed in *E. coli*, insect cells (e.g., using baculovirus expression vectors), yeast cells, or mammalian cells. Suitable host cells are discussed further by Goeddel (31). A recombinant expression vector can also be transcribed and translated in vitro, for example using T7 promoter regulatory sequences and T7 polymerase.

Expression of polypeptides in prokaryotes can be carried out in *E. coli* with vectors containing constitutive or inducible promoters directing the expression of either fusion or non-fusion polypeptides. Fusion vectors add a number of amino acids to a polypeptide. Such fusion vectors typically serve to increase expression of recombinant polypeptide, to increase the solubility of the recombinant polypeptide and/or to aid in the purification of the recombinant polypeptide by acting as a ligand during purification. Often, a proteolytic cleavage site is introduced at the junction of the fusion moiety and the recombinant polypeptide to enable separation of the recombinant polypeptide from the fusion moiety after purification of the fusion polypeptide. Such enzymes, and their cognate recognition sequences, include Factor Xa, thrombin and enterokinase. Typical fusion expression vectors include pGEX (Pharmacia Biotech Inc), pMAL (New England Biolabs, Beverly, Mass.) and pRIT5 (Pharmacia, Piscataway, N.J.) which fuse glutathione S-transferase (GST), maltose E binding polypeptide, or polypeptide A, respectively, to the target recombinant polypeptide.

Purified fusion polypeptides can be used in screening assays and to generate antibodies specific for polypeptides.

Expressing a polypeptide in host bacteria with an impaired capacity to proteolytically cleave the recombinant polypeptide can be used to maximize recombinant polypeptide expression (32). The nucleotide sequence of the nucleic acid to be inserted into an expression vector can be changed so that the individual codons for each amino acid are those preferentially utilized in *E. coli* (33).

When used in mammalian cells, the expression vector's control functions are often provided by viral regulatory elements. For example, commonly used promoters are derived from polyoma, Adenovirus 2, cytomegalovirus and Simian Virus 40. Recombinant mammalian expression vectors can be capable of directing expression of the nucleic acid in a particular cell type (e.g., tissue-specific regulatory elements are used to express the nucleic acid). Examples of suitable tissue-specific promoters include an albumin promoter(34), lymphoid-specific promoters (35) (36), promoters of immunoglobulins(37;38), neuron-specific promoters (39), pancreas-specific promoters (40), and mammary gland-specific promoters (e.g., milk whey promoter; U.S. Pat. No. 4,873,316 and European Application Publication No. 264,166). Developmentally-regulated promoters are sometimes utilized, for example, the murine hox promoters(41) and the .alpha.-feto-polypeptide promoter(42).

Vectors can be introduced into host cells via conventional transformation or transfection techniques. The terms transformation and transfection refer to a variety of techniques known for introducing foreign nucleic acid (e.g., DNA) into a host cell, including calcium phosphate or calcium chloride co-precipitation, transduction/infection, DEAE-dextran-mediated transfection, lipofection, or electroporation.

A host cell can be used to produce a polypeptide. Accordingly, methods for producing a polypeptide using the host cells are included as part of this invention. Such a method can include culturing host cells into which a recombinant expression vector encoding a polypeptide has been introduced in a suitable medium such that the polypeptide is produced. The method can further include isolating the polypeptide from the medium or the host cell.

Polypeptides can be expressed in transgenic animals or plants by introducing a nucleic acid encoding the polypeptide into the genome of an animal. In certain embodiments the nucleic acid is placed under the control of a tissue specific promoter, e.g., a milk or egg specific promoter, and recovered from the milk or eggs produced by the animal. Also included is a population of cells from a transgenic animal.

Isolated polypeptides encoded by a nucleotide sequence from SEQ ID NO: 1 or 3, or a fragment thereof, can be synthesized. Isolated polypeptides include both the full-length polypeptide and the mature polypeptide (i.e., the polypeptide minus the signal sequence or propeptide domain). An isolated, or purified, polypeptide or protein is substantially free of cellular material or other contaminating proteins from the cell or tissue source from which the protein is derived, or is substantially free from chemical precursors or other chemicals when chemically synthesized. Substantially free means a preparation of a polypeptide having less than about 5% (by dry weight) of contaminating protein, or of chemical precursors or non-target chemicals. When the desired polypeptide is recombinantly produced, it is typically substantially free of culture medium, specifically, where culture medium represents less than about 10% of the polypeptide preparation.

Also, polypeptides may exist as chimeric or fusion polypeptides. As used herein, a "target chimeric polypeptide"

or "target fusion polypeptide" includes a target polypeptide linked to a different polypeptide. The target polypeptide in the fusion polypeptide can correspond to an entire or nearly entire polypeptide as it exists in nature or a fragment thereof. The other polypeptide can be fused to the N-terminus or C-terminus of the target polypeptide.

Fusion polypeptides can include a moiety having high affinity for a ligand. For example, the fusion polypeptide can be a GST-target fusion polypeptide in which the target sequences are fused to the C-terminus of the GST sequences, or a polyhistidine-target fusion polypeptide in which the target polypeptide is fused at the N- or C-terminus to a string of histidine residues. Such fusion polypeptides can facilitate purification of recombinant target polypeptide. Expression vectors are commercially available that already encode a fusion moiety (e.g., a GST polypeptide), and a nucleotide sequence from SEQ ID NO: 1, 3 or 4, or a fragment thereof, or a substantially identical nucleotide sequence thereof, can be cloned into an expression vector such that the fusion moiety is linked in-frame to the target polypeptide. Further, the fusion polypeptide can be a target polypeptide containing a heterologous signal sequence at its N-terminus. In certain host cells (e.g., mammalian host cells), expression, secretion, cellular internalization, and cellular localization of a target polypeptide can be increased through use of a heterologous signal sequence. Fusion polypeptides can also include all or a part of a serum polypeptide (e.g., an IgG constant region or human serum albumin).

Target polypeptides can be used as immunogens to produce anti-target antibodies in a subject, to purify the polypeptide ligands or binding partners.

Polypeptides can be differentially modified during or after translation, e.g., by glycosylation, acetylation, phosphorylation, amidation, derivatization by known protecting/blocking groups, proteolytic cleavage, linkage to an antibody molecule or other cellular ligand, etc. Any known modification including specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc. may be used. Additional post-translational modifications include, for example, N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of prokaryotic host cell expression. The polypeptide fragments may also be modified with a detectable label, such as an enzymatic, fluorescent, isotopic or affinity label to allow for detection and isolation of the polypeptide.

Pharmacogenomics is a discipline that involves tailoring a treatment for a subject according to the subject's genotype. For example, based upon the outcome of a prognostic test, a clinician or physician may target pertinent information and preventative or therapeutic treatments to a subject who would be benefited by the information or treatment and avoid directing such information and treatments to a subject who would not be benefited (e.g., the treatment has no therapeutic effect and/or the subject experiences adverse side effects). As therapeutic approaches for age related macular degeneration continue to evolve and improve, the goal of treatments for age related macular degeneration related disorders is to intervene even before clinical signs manifest themselves. Thus, genetic markers associated with susceptibility to age related macular degeneration prove useful for early diagnosis, prevention and treatment of age related macular degeneration.

The following is an example of a pharmacogenomic embodiment. A particular treatment regimen can exert a differential effect depending upon the subject's genotype. Where a candidate therapeutic exhibits a significant beneficial interaction with a prevalent allele and a comparatively weak interaction with an uncommon allele (e.g., an order of magnitude or greater difference in the interaction), such a therapeutic typically would not be administered to a subject genotyped as being homozygous for the uncommon allele, and sometimes not administered to a subject genotyped as being heterozygous for the uncommon allele. In another example, where a candidate therapeutic is not significantly toxic when administered to subjects who are homozygous for a prevalent allele but is comparatively toxic when administered to subjects heterozygous or homozygous for an uncommon allele, the candidate therapeutic is not typically administered to subjects who are genotyped as being heterozygous or homozygous with respect to the uncommon allele.

Methods of the invention are applicable to pharmacogenomic methods for detecting, preventing, alleviating and/or treating age related macular degeneration. For example, a nucleic acid sample from an individual may be subjected to a genetic test. Where one or more polymorphic variants associated with increased risk of age related macular degeneration are identified at SNPs in the individual, information for detecting, preventing or treating age related macular degeneration and/or one or more age related macular degeneration detection, prevention and/or treatment regimens then may be directed to and/or prescribed to that individual.

In certain embodiments, a detection, preventative and/or treatment regimen is specifically prescribed and/or administered to individuals who will most benefit from it based upon their risk of developing age related macular degeneration assessed by the methods described herein. Methods are thus provided for identifying a subject at risk of age related macular degeneration and then prescribing a detection, therapeutic or preventative regimen to individuals identified as being at increased risk of age related macular degeneration. Thus, certain embodiments are directed to methods for treating age related macular degeneration in a subject, reducing risk of age related macular degeneration in a subject, or early detection of age related macular degeneration in a subject, which comprise: detecting the presence or absence of a polymorphic variant associated with age related macular degeneration at a SNP in a nucleotide sequence set forth in SEQ ID NOs:1 and 3, and prescribing or administering an age related macular degeneration treatment regimen, preventative regimen and/or detection regimen to a subject from whom the sample originated where the presence of polymorphic variants associated with age related macular degeneration are detected at one or more SNPs in the nucleotide sequence. In these methods, genetic results may be utilized in combination with other test results to diagnose age related macular degeneration as described above.

The use of certain age related macular degeneration treatments are known in the art, and include surgery, chemotherapy and/or radiation therapy. Any of the treatments may be used in combination to treat or prevent age related macular degeneration (e.g., surgery followed by radiation therapy or chemotherapy).

Pharmacogenomics methods also may be used to analyze and predict a response to a age related macular degeneration treatment or a drug. For example, if pharmacogenomics analysis indicates a likelihood that an individual will respond positively to a age related macular degeneration treatment with a particular drug, the drug may be administered to the individual. Conversely, if the analysis indicates that an individual is likely to respond negatively to treatment with a particular drug, an alternative course of treatment may be prescribed. A negative response may be defined as either the absence of an efficacious response or the presence of toxic side effects. The response to a therapeutic treatment can be predicted in a background study in which subjects in any of the following populations are genotyped: a population that responds favorably to a treatment regimen, a population that does not respond significantly to a treatment regimen, and a population that responds adversely to a treatment regiment (e.g., exhibits one or more side effects). These populations are provided as examples and other populations and subpopulations may be analyzed. Based upon the results of these analyses, a subject is genotyped to predict whether he or she will respond favorably to a treatment regimen, not respond significantly to a treatment regimen, or respond adversely to a treatment regimen.

The methods described herein also are applicable to clinical drug trials. Polymorphic variants indicative of response to an agent for treating age related macular degeneration or to side effects to an agent for treating age related macular degeneration may be identified at one or more SNPs. Thereafter, potential participants in clinical trials of such an agent may be screened to identify those individuals most likely to respond favorably to the drug and exclude those likely to experience side effects. In that way, the effectiveness of drug treatment may be measured in individuals who respond positively to the drug, without lowering the measurement as a result of the inclusion of individuals who are unlikely to respond positively in the study and without risking undesirable safety problems.

Thus, another embodiment is a method of selecting an individual for inclusion in a clinical trial of a treatment or drug comprising the steps of: (a) obtaining a nucleic acid sample from an individual; (b) determining the identity of a polymorphic variant which is associated with a positive response to the treatment or the drug, or a polymorphic variant which is associated with a negative response to the treatment or the drug at least one SNP in the nucleic acid sample, and (c) including the individual in the clinical trial if the nucleic acid sample contains the polymorphic variant associated with a positive response to the treatment or the drug or if the nucleic acid sample lacks said polymorphic variant associated with a negative response to the treatment or the drug. The SNP may be in a sequence selected individually or in any combination from the C3 genomic sequence disclosed in the table. Step (c) can also include administering the drug or the treatment to the individual if the nucleic acid sample contains the polymorphic variant associated with a positive response to the treatment or the drug and the nucleic acid sample lacks the polymorphic variant associated with a negative response to the treatment or the drug.

A peptide nucleic acid, or PNA, refers to a nucleic acid mimic such as a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. Synthesis of PNA oligomers can be performed using standard solid phase peptide synthesis protocols as described, for example, in Hyrup et al. (71), and Perry-O'Keefe et al.(70).

PNA nucleic acids can be used in prognostic and diagnostic applications. For example, PNAs can be used in the analysis of SNPs in a gene, (e.g., by PNA-directed PCR clamping); as artificial restriction enzymes when used in combination with other enzymes, (e.g., S1 nucleases(71) or as probes or primers for DNA sequencing or hybridization (71;72).

A further aspect of the invention provides an antibody molecule that binds specifically to a variant C3 polypeptide i.e. a polypeptide encoded by a nucleotide sequence comprising polymorphic variants at one or more SNPs described herein. For example, an antibody molecule may bind specifically to the C3F polypeptide which comprises an R102G substitution which is encoded by the coding sequence comprising the G allele of SNP rs2230199. Such an antibody binds preferentially to the C3F polypeptide relative to C3S polypeptide which lacks the R102G substitution.

A method of identifying and/or obtaining an antibody specific for C3F polypeptide may comprise;
  providing a population of antibody molecules specific for C3F polypeptide,
  contacting said population with a C3S polypeptide,
  identifying one or more members of said population which bind preferentially to C3F relative to C3S polypeptide.

Antibody molecules may be useful both in the diagnosis of AMD, in accordance with the invention.

Antibodies that are specific for a C3 polypeptide may be obtained using techniques that are standard in the art. An immunogen typically is used to prepare antibodies by immunizing a suitable subject, (e.g., rabbit, goat, mouse or other mammal). An appropriate immunogenic preparation can contain, for example, recombinantly expressed chemically synthesized polypeptide. The preparation can further include an adjuvant, such as Freund's complete or incomplete adjuvant, or a similar immunostimulatory agent.

Amino acid polymorphisms can be detected using antibodies specific for the altered epitope by western analysis after the electrophoresis of denatured proteins. Protein polymorphism can also be detected using fluorescently identified antibodies which bind to specific polymorphic epitopes and detected in whole cells using fluorescence activated cell sorting techniques (FACS). Polymorphic protein sequence may also be determined by NMR spectroscopy or by x-ray diffraction studies. Further, determination of polymorphic sites in proteins may be accomplished by observing differential cleavage by specific or non specific proteases.

An antibody is an immunoglobulin molecule or immunologically active portion thereof, i.e., an antigen-binding portion. Examples of immunologically active portions of immunoglobulin molecules include F(ab) and F(ab')$_2$ fragments which can be generated by treating the antibody with an enzyme such as pepsin. An antibody can be polyclonal, monoclonal, or recombinant (e.g., a chimeric or humanized), fully human, non-human (e.g., murine), or a single chain antibody.

A full-length polypeptide or antigenic peptide fragment encoded by a target nucleotide sequence can be used as an immunogen or can be used to identify antibodies made with other immunogens, e.g., cells, membrane preparations, and the like. An antigenic peptide often includes at least 8 amino acid residues of the amino acid sequences encoded by a nucleotide sequence of one of SEQ ID NOs:1 and 3, and encompasses an epitope. Antigenic peptides sometimes include 10 or more amino acids, 15 or more amino acids, 20 or more amino acids, or 30 or more amino acids. Hydrophilic and hydrophobic fragments of polypeptides sometimes are used as immunogens.

Epitopes encompassed by the antigenic peptide are regions located on the surface of the polypeptide (e.g., hydrophilic regions) as well as regions with high antigenicity. For example, an Emini surface probability analysis of the human polypeptide sequence can be used to indicate the regions that have a particularly high probability of being localized to the surface of the polypeptide and are thus likely to constitute surface residues useful for targeting antibody production. The antibody may bind an epitope on any domain or region on polypeptides for use in the invention.

An antibody (e.g., monoclonal antibody) can be used to isolate target polypeptides by standard techniques, such as affinity chromatography or immunoprecipitation. Moreover, an antibody can be used to detect a target polypeptide (e.g., in a cellular lysate or cell supernatant) in order to evaluate the abundance and pattern of expression of the polypeptide. Antibodies can be used diagnostically to monitor polypeptide levels in tissue as part of a clinical testing procedure, e.g., to determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H. Also, an antibody can be utilized as a test molecule for determining whether it can treat age related macular degeneration, and as a therapeutic for administration to a subject for treating age related macular degeneration.

An antibody can be made by immunizing with a purified antigen, or a fragment thereof, a membrane associated antigen, tissues, e.g., crude tissue preparations, whole cells, preferably living cells, lysed cells, or cell fractions.

Included as part of this invention are antibodies which bind only a native polypeptide, only denatured or otherwise non-native polypeptide, or which bind both, as well as those having linear or conformational epitopes. Conformational epitopes sometimes can be identified by selecting antibodies that bind to native but not denatured polypeptide. Also featured are antibodies that specifically bind to a polypeptide variant associated with age related macular degeneration.

Preferably, an antibody displays increased binding to the C3F polypeptide relative to the C3S polypeptide.

The examples set forth below are intended to illustrate but not limit the invention.

Age-related macular degeneration is the most common cause of blindness in Western populations. Susceptibility is influenced by age and by genetic and environmental factors. Complement activation is implicated in the pathogenesis. We tested for an association between age-related macular degeneration and 13 single nucleotide polymorphisms (SNPs) spanning the complement genes C3 and C5 in case subjects and control subjects from the southeastern region of England. All subjects were examined by an ophthalmologist and had independent grading of fundus photographs to confirm their disease status. To test for replication of the most significant findings, we genotyped a set of Scottish cases and controls. The common functional polymorphism rs2230199 (Arg102Gly) in the C3 gene, corresponding to the electrophoretic variants C3S (slow) and C3F (fast), was strongly associated with age-related macular degeneration in both the English group (603 cases and 350 controls, P=5.9×1-5) and the Scottish group (244 cases and 351 controls, P=5.0×10-5). The odds ratio for age-related macular degeneration in C3 S/F heterozygotes as compared with S/S homozygotes was 1.7 (95% confidence interval [CI], 1.3 to 2.1); for F/F homozygotes, the odds ratio was 2.6 (95% CI, 1.6 to 4.1). The estimated population attributable risk for C3F was 22%. Complement C3 is important in the pathogenesis of age-related macular degeneration. This finding further underscores the influence of the complement pathway in the pathogenesis of this disease.

The inventors of the present invention have discovered a single base pair polymorphism that is present in a highly significant percentage of the genetic DNA of individuals affected with age related macular degeneration while only present in a smaller percentage of individuals who are not known to be affected by the disease.

For individuals with age-related macular degeneration, the distribution of polymorphic alleles at position 6669387 of chromosome 19, found within the C3 gene, was different from those without age-related macular degeneration (Table 1). The trend test for risk associated with carrying the C allele (on the positive reference strand of the human genome) had an empirical p-value of 0.000059225, and the corresponding Mantel-Haenszel odds ratio for trend is 1.600 (Table 1). These data further suggest that this marker, located within the C3 gene, is associated with age-related macular degeneration risk and that the C allele at position 6669387 of chromosome 19 is associated with an increased risk of developing age-related macular degeneration. The C allele at position 6669387 of the positive strand corresponds to the G allele within the negative strand, in which is found the coding sequence for C3.

TABLE 1

| rs no. | 2230199 |
|---|---|
| Chromosome; Position | 19; 6669387 |
| Gene Name | C3 |
| SEQ ID NO; Position | 3; 2274 |
| Genotype; Phenotype | n = C; increased risk (positive strand relative to the human reference sequence version 36.1) |
| Hardy-Weinberg | 0.86594 |

| Case Flag | Allele B | AA | AB | BB | Model | p-Value | Odds Ratio |
|---|---|---|---|---|---|---|---|
| 0 | C | 223 | 109 | 14 | Trend | 0.000059 | 1.600 |
| 1 | C | 303 | 242 | 45 | | | |

The present invention has been described in detail by way of illustration and example in order to acquaint others skilled in the art with the invention, its principles and its practical application. Particular formulations and processes of the present invention are not limited to the descriptions of the specific embodiments presented, but rather the descriptions and examples should be viewed in terms of the claims that follow and their equivalents. While some of the examples and descriptions above include some conclusions about the way the invention may function, the inventors do not intend to be bound by those conclusions and functions, but put them forth only as possible explanations.

It is to be further understood that the specific embodiments of the present invention as set forth are not intended as being exhaustive or limiting of the invention, and that many alternatives, modifications and variations will be apparent to those of ordinary skill in the art in light of the foregoing examples and detailed description. Accordingly, this invention is intended to embrace all such alternatives, modifications and variations that fall within the spirit and scope of the following claims.

REFERENCE LIST (1) Swaroop A, Branham K E, Chen W, Abecasis G. Genetic susceptibility to age-related macular degeneration: a paradigm for dissecting complex disease traits. Hum Mol Genet. 2007 Oct. 15; 16 Spec No 2:R174-82:R174-R182.
(2) Ambati J, Ambati B K, Yoo S H, Ianchulev S, Adamis A P. Age-related macular degeneration: etiology, pathogenesis, and therapeutic strategies. Surv Opthalmol 2003 May; 48(3):257-93.
(3) Klaver C C, Wolfs R C, Vingerling J R, Hofman A, de Jong P T. Age-specific prevalence and causes of blindness and visual impairment in an older population: the Rotterdam Study. Arch Opthalmol 1998 May; 116(5):653-8.
(4) Hammond C J, Webster A R, Snieder H, Bird A C, Gilbert C E, Spector T D. Genetic influence on early age-related maculopathy: a twin study. Opthalmology 2002 April; 109(4):730-6.
(5) Heiba I M, Elston R C, Klein B E, Klein R. Sibling correlations and segregation analysis of age-related maculopathy: the Beaver Dam Eye Study. Genet Epidemiol 1994; 11(1):51-67.
(6) Smith W, Assink J, Klein R, Mitchell P, Klaver C C, Klein B E, et al. Risk factors for age-related macular degeneration: Pooled findings from three continents. Opthalmology 2001 April; 108(4):697-704.
(7) van L R, Klaver C C, Vingerling J R, Hofman A, de Jong P T. Epidemiology of age-related maculopathy: a review. Eur J Epidemiol 2003; 18(9):845-54.
(8) Huang G H, Klein R, Klein B E, Tomany S C. Birth cohort effect on prevalence of age-related maculopathy in the Beaver Dam Eye Study. Am J Epidemiol 2003 April 15; 157(8):721-9.
(9) Haines J L, Hauser M A, Schmidt S, Scott W K, Olson L M, Gallins P, et al. Complement factor H variant increases the risk of age-related macular degeneration. Science 2005 Apr. 15; 308(5720):419-21.
(10) Hageman G S, Anderson D H, Johnson L V, Hancox L S, Taiber A J, Hardisty L I, et al. A common haplotype in the complement regulatory gene factor H(HF1/CFH) predisposes individuals to age-related macular degeneration. Proc Natl Acad Sci USA 2005 May 17; 102(20):7227-32.
(11) Klein R J, Zeiss C, Chew E Y, Tsai J Y, Sackler R S, Haynes C, et al. Complement factor H polymorphism in age-related macular degeneration. Science 2005 Apr. 15; 308(5720):385-9.
(12) Edwards A O, Ritter R, III, Abel K J, Manning A, Panhuysen C, Farrer L A. Complement factor H polymorphism and age-related macular degeneration. Science 2005 Apr. 15; 308(5720):421-4.
(13) Zareparsi S, Branham K E, Li M, Shah S, Klein R J, Ott J, et al. Strong association of the Y402H variant in complement factor H at 1q32 with susceptibility to age-related macular degeneration. Am J Hum Genet. 2005 Jul.; 77(1): 149-53.
(14) Jakobsdottir J, Conley Y P, Weeks D E, Mah T S, Ferrell R E, Gorin M B. Susceptibility genes for age-related maculopathy on chromosome 10q26. Am J Hum Genet. 2005 September.; 77(3):389-407.
(15) Li M, tmaca-Sonmez P, Othman M, Branham K E, Khanna R, Wade M S, et al. CFH haplotypes without the Y402H coding variant show strong association with susceptibility to age-related macular degeneration. Nat Genet. 2006 September.; 38(9):1049-54.
(16) Rivera A, Fisher S A, Fritsche L G, Keilhauer C N, Lichtner P, Meitinger T, et al. Hypothetical LOC387715 is a second major susceptibility gene for age-related macular degeneration, contributing independently of complement factor H to disease risk. Hum Mol Genet. 2005 Nov. 1; 14(21):3227-36.
(17) DeWan A, Liu M, Hartman S, Zhang S S, Liu D T, Zhao C, et al. HTRA1 promoter polymorphism in wet age-related macular degeneration. Science 2006 Nov. 10; 314(5801):989-92.
(18) Yang Z, Camp N J, Sun H, Tong Z, Gibbs D, Cameron D J, et al. A variant of the HTRA1 gene increases susceptibility to age-related macular degeneration. Science 2006 Nov. 10; 314(5801):992-3.
(19) Kanda A, Chen W, Othman M, Branham K E, Brooks M, Khanna R, et al. A variant of mitochondrial protein LOC387715/ARMS2, not HTRA1, is strongly associated with age-related macular degeneration. Proc Natl Acad Sci USA 2007 Oct. 9; 104(41):16227-32.
(20) Gold B, Merriam J E, Zemant J, Hancox L S, Taiber A J, Gehrs K, et al. Variation in factor B (BF) and complement component 2 (C2) genes is associated with age-related macular degeneration. Nat Genet. 2006 April; 38(4):458-62.
(21) Yates J R, Sepp T, Matharu B K, Khan J C, Thurlby D A, Shahid H, et al. Complement C3 variant and the risk of age-related macular degeneration. N Engl J Med 2007 Aug. 9; 357(6):553-61.
(22) Maller J B, Fagerness J A, Reynolds R C, Neale B M, Daly M J, Seddon J M. Variation in complement factor 3 is associated with risk of age-related macular degeneration. Nat Genet. 2007 October; 39(10):1200-1.
(23) Johnson G C, Esposito L, Barratt B J, Smith A N, Heward J, Di G G, et al. Haplotype tagging for the identification of common disease genes. Nat Genet. 2001 October; 29(2): 233-7.
(24) Sasieni P D. From genotypes to genes: doubling the sample size. Biometrics 1997 December; 53(4):1253-61.
(25) Saiki R K, Bugawan T L, Horn G T, Mullis K B, Erlich H A. Analysis of enzymatically amplified beta-globin and HLA-DQ alpha DNA with allele-specific oligonucleotide probes. Nature 1986 Nov. 13; 324(6093):163-6.
(26) Myers R M, Larin Z, Maniatis T. Detection of single base substitutions by ribonuclease cleavage at mismatches in RNA:DNA duplexes. Science 1985 Dec. 13; 230(4731): 1242-6.
(27) Cotton R G, Rodrigues N R, Campbell R D. Reactivity of cytosine and thymine in single-base-pair mismatches with hydroxylamine and osmium tetroxide and its application to the study of mutations. Proc Natl Acad Sci USA 1988 June; 85(12):4397-401.
(28) Cronin M T, Fucini R V, Kim S M, Masino R S, Wespi R M, Miyada C G. Cystic fibrosis mutation detection by hybridization to light-generated DNA probe arrays. Hum Mutat 1996; 7(3):244-55.
(29) Kozal M J, Shah N, Shen N, Yang R, Fucini R, Merigan T C, et al. Extensive polymorphisms observed in HIV-1 clade B protease gene using high-density oligonucleotide arrays. Nat Med 1996 July; 2(7):753-9.
(30) Agresti A. Exact inference for categorical data: recent advances and continuing controversies. Stat Med 2001 Sep. 15; 20(17-18):2709-22.
(31) Goeddel D V. Systems for heterologous gene expression. Methods Enzymol 1990; 185:3-7:3-7.
(32) Gottesman S. Minimizing proteolysis in *Escherichia coli*: genetic solutions. Methods Enzymol 1990; 185:119-29:119-29.
(33) Wada K, Wada Y, Ishibashi F, Gojobori T, Ikemura T. Codon usage tabulated from the GenBank genetic sequence data. Nucleic Acids Res 1992 May 11; 20 Suppl: 2111-8:2111-8.
(34) Pinkert C A, Ornitz D M, Brinster R L, Palmiter R D. An albumin enhancer located 10 kb upstream functions along with its promoter to direct efficient, liver-specific expression in transgenic mice. Genes Dev 1987 May; 1 (3):268-76.

(35) Calame K, Eaton S. Transcriptional controlling elements in the immunoglobulin and T cell receptor loci. Adv Immunol 1988; 43:235-75:235-75.

(36) Winoto A, Baltimore D. A novel, inducible and T cell-specific enhancer located at the 3' end of the T cell receptor alpha locus. EMBO J. 1989 March; 8(3):729-33.

(37) Banerji J, Olson L, Schaffner W. A lymphocyte-specific cellular enhancer is located downstream of the joining region in immunoglobulin heavy chain genes. Cell 1983 July; 33(3):729-40.

(38) Queen C, Baltimore D. Immunoglobulin gene transcription is activated by downstream (sequence elements. Cell 1983 July; 33(3):741-8.

(39) Byrne G W, Ruddle F H. Multiplex gene regulation: a two-tiered approach to transgene regulation in transgenic mice. Proc Natl Acad Sci USA 1989 July; 86(14):5473-7.

(40) Edlund T, Walker M D, Barr P J, Rutter W J. Cell-specific expression of the rat insulin gene: evidence for role of two distinct 5' flanking elements. Science 1985 Nov. 22; 230 (4728):912-6.

(41) Kessel M, Gruss P. Murine developmental control genes. Science 1990 Jul. 27; 249(4967):374-9.

(42) Camper S A, Tilghman S M. Postnatal repression of the alpha-fetoprotein gene is enhancer independent. Genes Dev 1989 April; 3(4):537-46.

(43) Malik F, Delgado C, Knusli C, Irvine A E, Fisher D, Francis G E. Polyethylene glycol (PEG)-modified granulocyte-macrophage colony-stimulating factor (GM-CSF) with conserved biological activity. Exp Hematol 1992 September; 20(8):1028-35.

(44) Zuckermann R N, Martin E J, Spellmeyer D C, Stauber G B, Shoemaker K R, Kerr J M, et al. Discovery of nanomolar ligands for 7-transmembrane G-protein-coupled receptors from a diverse N-(substituted)glycine peptoid library. J Med Chem 1994 August; %19; 37(17):2678-85.

(45) Lam K S. Application of combinatorial library methods in cancer research and drug discovery. Anticancer Drug Des 1997 April; 12(3):145-67.

(46) DeWitt S H, Kiely J S, Stankovic C J, Schroeder M C, Cody D M, Pavia M R. "Diversomers": an approach to nonpeptide, nonoligomeric chemical diversity. Proc Natl Acad Sci USA 1993 Aug. 1; 90(15):6909-13.

(47) Erb E, Janda K D, Brenner S. Recursive deconvolution of combinatorial chemical libraries. Proc Natl Acad Sci USA 1994 Nov. 22; 91(24):11422-6.

(48) Cho C Y, Moran E J, Chemy S R, Stephans J C, Fodor S P, Adams C L, et al. An unnatural biopolymer. Science 1993 Sep. 3; 261(5126):1303-5.

(49) Gallop M A, Barrett R W, Dower W J, Fodor S P, Gordon E M. Applications of combinatorial technologies to drug discovery. 1. Background and peptide combinatorial libraries. J Med Chem 1994 Apr. 29; 37(9):1233-51.

(50) Houghten R A, Appel J R, Blondelle S E, Cuervo J H, Dooley C T, Pinilla C. The use of synthetic peptide combinatorial libraries for the identification of bioactive peptides. Biotechniques 1992 September; 13(3):412-21.

(51) Lam K S, Salmon S E, Hersh E M, Hruby V J, Kazmierski W M, Knapp R J. A new type of synthetic peptide library for identifying ligand-binding activity. Nature 1991 Nov. 7; 354(6348):82-4.

(52) Fodor S P, Rava R P, Huang X C, Pease A C, Holmes C P, Adams C L. Multiplexed biochemical assays with biological chips. Nature 1993 Aug. 5; 364(6437):555-6.

(53) Cull M G, Miller J F, Schatz P J. Screening for receptor ligands using large libraries of peptides linked to the C terminus of the lac repressor. Proc Natl Acad Sci USA 1992 Mar. 1; 89(5):1865-9.

(54) Scott J K, Smith G P. Searching for peptide ligands with an epitope library. Science 1990 Jul. 27; 249(4967):386-90.

(55) Devlin J J, Panganiban L C, Devlin P E. Random peptide libraries: a source of specific protein binding molecules. Science 1990 Jul. 27; 249(4967):404-6.

(56) Cwirla S E, Peters E A, Barrett R W, Dower W J. Peptides on phage: a vast library of peptides for identifying ligands. Proc Natl Acad Sci USA 1990 August; 87(16):6378-82.

(57) Felici F, Castagnoli L, Musacchio A, Jappelli R, Cesareni G. Selection of antibody ligands from a large library of oligopeptides expressed on a multivalent exposition vector. J Mol Biol 1991 November; %20; 222(2):301-10.

(58) Gautier C, Morvan F, Rayner B, Huynh-Dinh T, Igolen J, Imbach J L, et al. Alpha-DNA. IV: Alpha-anomeric and beta-anomeric tetrathymidylates covalently linked to intercalating oxazolopyridocarbazole. Synthesis, physicochemical properties and poly (rA) binding. Nucleic Acids Res 1987 Aug. 25; 15(16):6625-41.

(59) Inoue H, Hayase Y, Imura A, Iwai S, Miura K, Ohtsuka E. Synthesis and hybridization studies on two complementary nona(2'-O-methyl)ribonucleotides. Nucleic Acids Res 1987 Aug. 11; 15(15):6131-48.

(60) Inoue H, Hayase Y, Iwai S, Ohtsuka E. Sequence-dependent hydrolysis of RNA using modified oligonucleotide splints and RNase H. FEBS Lett 1987 May 11; 215(2):327-30.

(61) Haseloff J, Gerlach W L. Simple RNA enzymes with new and highly specific endoribonuclease activities. Nature 1988 Aug. 18; 334(6183):585-91.

(62) Bartel D P, Szostak J W. Isolation of new ribozymes from a large pool of random sequences [see comment]. Science 1993 Sep. 10; 261(5127):1411-8.

(63) Helene C. The anti-gene strategy: control of gene expression by triplex-forming-oligonucleotides. Anticancer Drug Des 1991 December; 6(6):569-84.

(64) Helene C, Thuong N T, Harel-Bellan A. Control of gene expression by triple helix-forming oligonucleotides. The antigene strategy. Ann NY Acad Sci 1992 Oct. 28; 660:27-36:27-36.

(65) Maher L J, III. DNA triple-helix formation: an approach to artificial gene repressors? Bioessays 1992 December; 14(12):807-15.

(66) Bosher J M, Labouesse M. RNA interference: genetic wand and genetic watchdog. Nat Cell Biol 2000 February; 2(2):E31-E36.

(67) Caplen N J, Parrish S, Imani F, Fire A, Morgan R A. Specific inhibition of gene expression by small double-stranded RNAs in invertebrate and vertebrate systems. Proc Natl Acad Sci USA 2001 Aug. 14; 98(17):9742-7.

(68) Elbashir S M, Harborth J, Weber K, Tuschl T. Analysis of gene function in somatic mammalian cells using small interfering RNAs. Methods 2002 February; 26(2):199-213.

(69) Caplen N J, Parrish S, Imani F, Fire A, Morgan R A. Specific inhibition of gene expression by small double-stranded RNAs in invertebrate and vertebrate systems. Proc Natl Acad Sci USA 2001 Aug. 14; 98(17):9742-7.

(70) Abderrahmani A, Steinmann M, Plaisance V, Niederhauser G, Haefliger J A, Mooser V, et al. The transcriptional repressor REST determines the cell-specific expression of the human MAPK8IP1 gene encoding IB1 (JIP-1). Mol Cell Biol 2001 November; 21(21):7256-67.

(71) Hyrup B, Nielsen P E. Peptide nucleic acids (PNA): synthesis, properties and potential applications. Bioorg Med Chem 1996 January; 4(1):5-23.

(72) Perry-O'Keefe H, Yao X W, Coull J M, Fuchs M, Egholm M. Peptide nucleic acid pre-gel hybridization: an alternative to southern hybridization. Proc Natl Acad Sci USA 1996 Dec. 10; 93(25):14670-5.

(73) Letsinger R L, Zhang G R, Sun D K, Ikeuchi T, Sarin P S. Cholesteryl-conjugated oligonucleotides: synthesis, properties, and activity as inhibitors of replication of human immunodeficiency virus in cell culture. Proc Natl Acad Sci USA 1989 September; 86(17):6553-6.

(74) Lemaitre M, Bayard B, Lebleu B. Specific antiviral activity of a poly(L-lysine)-conjugated oligodeoxyribonucleotide sequence complementary to vesicular stomatitis virus N protein mRNA initiation site. Proc Natl Acad Sci USA 1987 February; 84(3):648-52.

(75) van der Krol A R, Mol J N, Stuitje A R. Modulation of eukaryotic gene expression by complementary RNA or DNA sequences. Biotechniques 1988 November; 6(10):958-76.

(76) Zon G. Oligonucleotide analogues as potential chemotherapeutic agents. Pharm Res 1988 September; 5(9):539-49.

(77) Better M, Chang C P, Robinson R R, Horwitz A H. Escherichia coli secretion of an active chimeric antibody fragment. Science 1988 May; %20; 240(4855):1041-3.

(78) Liu A Y, Robinson R R, Hellstrom K E, Murray E D, Jr., Chang C P, Hellstrom I. Chimeric mouse-human IgG1 antibody that can mediate lysis of cancer cells. Proc Natl Acad Sci USA 1987 May; 84(10):3439-43.

(79) Liu A Y, Robinson R R, Murray E D, Jr., Ledbetter J A, Hellstrom I, Hellstrom K E. Production of a mouse-human chimeric monoclonal antibody to CD20 with potent Fc-dependent biologic activity. J Immunol 1987 Nov. 15; 139(10):3521-6.

(80) Sun L K, Curtis P, Rakowicz-Szulczynska E, Ghrayeb J, Chang N, Morrison S L, et al. Chimeric antibody with human constant regions and mouse variable regions directed against carcinoma-associated antigen 17-1A. Proc Natl Acad Sci USA 1987 January; 84(1):214-8.

(81) Nishimura Y, Yokoyama M, Araki K, Ueda R, Kudo A, Watanabe T. Recombinant human-mouse chimeric monoclonal antibody specific for common acute lymphocytic leukemia antigen. Cancer Res 1987 Feb. 15; 47(4):999-1005.

(82) Wood C R, Boss M A, Kenten J H, Calvert J E, Roberts N A, Emtage J S. The synthesis and in vivo assembly of functional antibodies in yeast. Nature 1985 Apr. 4; 314(6010):446-9.

(83) Shaw D R, Khazaeli M B, LoBuglio A F. Mouse/human chimeric antibodies to a tumor-associated antigen: biologic activity of the four human IgG subclasses. J Natl Cancer Inst 1988 Dec. 7; 80(19):1553-9.

(84) Morrison S L. Transfectomas provide novel chimeric antibodies. Science 1985 September; %20; 229(4719):1202-7.

(85) Verhoeyen M, Milstein C, Winter G. Reshaping human antibodies: grafting an antilysozyme activity. Science 1988 Mar. 25; 239(4847):1534-6.

(86) Beidler C B, Ludwig J R, Cardenas J, Phelps J, Papworth C G, Melcher E, et al. Cloning and high level expression of a chimeric antibody with specificity for human carcinoembryonic antigen. J Immunol 1988 Dec. 1; 141(11):4053-60.

(87) Lonberg N, Huszar D. Human antibodies from transgenic mice. Int Rev Immunol 1995; 13(1):65-93.

(88) Jespers L S, Roberts A, Mahler S M, Winter G, Hoogenboom H R. Guiding the selection of human antibodies from phage display repertoires to a single epitope of an antigen. Biotechnology (NY) 1994 September; 12(9):899-903.

(89) Colcher D, Pavlinkova G, Beresford G, Booth B J, Batra S K. Single-chain antibodies in pancreatic cancer. Ann NY Acad Sci 1999 Jun. 30; 880:263-80:263-80.

(90) Reiter Y, Pastan I. Antibody engineering of recombinant Fv immunotoxins for improved targeting of cancer: disulfide-stabilized Fv immunotoxins. Clin Cancer Res 1996 February; 2(2):245-52.

(91) McConnell H M, Owicki J C, Parce J W, Miller D L, Baxter G T, Wada H G, et al. The cytosensor microphysiometer: biological applications of silicon technology. Science 1992 Sep. 25; 257(5078):1906-12.

(92) Sjolander S, Urbaniczky C. Integrated fluid handling system for biomolecular interaction analysis. Anal Chem 1991 Oct. 15; 63(20):2338-45.

(93) Szabo A, Stolz L, Granzow R. Surface plasmon resonance and its use in biomolecular interaction analysis (BIA). Curr Opin Struct Biol 1995 October; 5(5):699-705.

(94) Rivas G, Minton A P. New developments in the study of biomolecular associations via sedimentation equilibrium. Trends Biochem Sci 1993 August; 18(8):284-7.

(95) Current Protocols in Molecular Biology. New York: Wiley; 1999.

(96) Heegaard N H. Capillary electrophoresis for the study of affinity interactions. J Mol Recognit 1998; 11(1-6):141-8.

(97) Zervos A S, Gyuris J, Brent R. Mxi1, a protein that specifically interacts with Max to bind Myc-Max recognition sites. Cell 1993 Jan. 29; 72(2):223-32.

(98) Madura K, Dohmen R J, Varshavsky A. N-recognin/Ubc2 interactions in the N-end rule pathway. J Biol Chem 1993 Jun. 5; 268(16):12046-54.

(99) Bartel P, Chien C T, Stemglanz R, Fields S. Elimination of false positives that arise in using the two-hybrid system. Biotechniques 1993 June; 14(6):920-4.

(100) Iwabuchi K, Li B, Bartel P, Fields S. Use of the two-hybrid system to identify the domain of p53 involved in oligomerization. Oncogene 1993 June; 8(6):1693-6.

(101) Remington's Pharmaceutical Sciences. Mack; 2005.

(102) Cruikshank W W, Doctrow S R, Falvo M S, Huffman K, Maciaszek J, Viglianti G, et al. A lipidated anti-Tat antibody enters living cells and blocks HIV-1 viral replication. J Acquir Immune Defic Syndr Hum Retrovirol 1997 Mar. 1; 14(3):193-203.

(103) Chen S H, Shine H D, Goodman J C, Grossman R G, Woo S L. Gene therapy for brain tumors: regression of experimental gliomas by adenovirus-mediated gene transfer in vivo. Proc Natl Acad Sci USA 1994 Apr. 12; 91(8):3054-7.

(104) Osborne S E, Matsumura I, Ellington A D. Aptamers as therapeutic and diagnostic reagents: problems and prospects. Curr Opin Chem Biol 1997 June; 1(1):5-9.

(105) Patel D J. Structural analysis of nucleic acid aptamers. Curr Opin Chem Biol 1997 June; 1(1):32-46.

(106) Herlyn D, Birebent B. Advances in cancer vaccine development. Ann Med 1999 February; 31(1):66-78.

(107) Bhattacharya-Chatterjee M, Foon K A. Anti-idiotype antibody vaccine therapies of cancer. Cancer Treat Res 1998; 94:51-68:51-68.

The invention claimed is:

1. A method for identifying an individual who has an increased risk for developing age-related macular degeneration (AMD) comprising;
   obtaining a biological sample from said individual, said individual being a human; and
   assaying DNA in said sample and detecting the presence of (i) at least one allele of the complement component 3 (C3) gene comprising a G nucleotide at the single nucleotide polymorphism (SNP) rs2230199 at the position corresponding to position 366 of SEQ ID NO: 1; or (ii) a C3 protein comprising a glycine amino acid at the position corresponding to position 102 of SEQ ID NO: 2;
   wherein the presence of at least one allele of the C3 gene comprising a G nucleotide at the single nucleotide polymorphism (SNP) rs2230199 at the position corresponding to position 366 of SEQ ID NO: 1 or a C3 protein comprising a glycine amino acid at the position corresponding to position 102 of SEQ ID NO: 2 is indicative of an increased risk of development of macular degeneration in the individual.

2. The method of claim 1 wherein said assaying comprises: amplifying the DNA in the presence of a pair of primers wherein a first primer comprises at least 10 consecutive nucleotides of one of SEQ ID NO: 1 or the complement of SEQ ID NO: 1 and is located upstream of the base located at position 366 of SEQ ID NO: 1, and a second primer comprises at least 10 consecutive nucleotides of the other of SEQ ID NO: 1 or the complement of SEQ ID NO: 1 and is located downstream of the base located at position 366 of SEQ ID NO: 1; and
   determining the identity of the base in the amplified genetic material that corresponds to position 366 of SEQ ID NO: 1.

* * * * *

UNITED STATES PATENT AND TRADEMARK OFFICE
CERTIFICATE OF CORRECTION

| | |
|---|---|
| PATENT NO. | : 8,114,592 B2 |
| APPLICATION NO. | : 12/382569 |
| DATED | : February 14, 2012 |
| INVENTOR(S) | : John R. W. Yates |

It is certified that error appears in the above-identified patent and that said Letters Patent is hereby corrected as shown below:

Column 64, line 19: "$P=5.9\times1-5$" should read --$P=5.9\times10-5$--.

Signed and Sealed this

Thirtieth Day of October, 2012

David J. Kappos
*Director of the United States Patent and Trademark Office*

SEQUENCE LISTING

<160> NUMBER OF SEQ ID NOS: 3

<210> SEQ ID NO 1
<211> LENGTH: 5101
<212> TYPE: DNA
<213> ORGANISM: Homo sapiens

<400> SEQUENCE: 1

```
cactcctccc catcctctcc ctctgtccct ctgtccctct gaccctgcac tgtcccagca     60
ccatgggacc cacctcaggt cccagcctgc tgctcctgct actaacccac ctccccctgg    120
ctctggggag tcccatgtac tctatcatca ccccccaacat cttgcggctg gagagcgagg   180
agaccatggt gctggaggcc cacgacgcgc aaggggatgt tccagtcact gttactgtcc    240
acgacttccc aggcaaaaaa ctagtgctgt ccagtgagaa gactgtgctg acccctgcca    300
ccaaccacat gggcaacgtc accttcacga tcccagccaa cagggagttc aagtcagaaa    360
aggggcgcaa caagttcgtg accgtgcagg ccaccttcgg gacccaagtg gtggagaagg    420
tggtgctggt cagcctgcag agcgggtacc tcttcatcca gacagacaag accatctaca    480
ccctggctc cacagttctc tatcggatct tcaccgtcaa ccacaagctg ctacccgtgg    540
gccgacggt catggtcaac attgagaacc cggaaggcat cccggtcaag caggactcct    600
tgtcttctca gaaccagctt ggcgtcttgc ccttgtcttg ggacattccg gaactcgtca    660
acatgggcca gtggaagatc cgagcctact atgaaaactc accacagcag gtcttctcca    720
ctgagtttga ggtgaaggag tacgtgctgc ccagtttcga ggtcatagtg gagcctacag    780
agaaattcta ctacatctat aacgagaagg gcctggaggt caccatcacc gccaggttcc    840
tctacgggaa gaaagtggag ggaactgcct ttgtcatctt cgggatccag gatggcgaac    900
agaggatttc cctgcctgaa tccctcaagc gcattccgat tgaggatggc tcggggggagg    960
ttgtgctgag ccggaaggta ctgctggacg gggtgcagaa cccccgagca aagacctgg   1020
tggggaagtc tttgtacgtg tctgccaccg tcatcttgca ctcaggcagt gacatggtgc   1080
aggcagagcg cagcgggatc cccatcgtga cctctcccta ccagatccac ttcaccaaga   1140
cacccaagta cttcaaacca ggaatgcccct ttgacctcat ggtgttcgtg acgaaccctg   1200
atggctctcc agcctaccga gtccccgtgg cagtccaggg cgaggacact gtgcagtctc   1260
taacccaggg agatggcgtg ccaaactca gcatcaacac acaccccagc cagaagccct   1320
tgagcatcac ggtgcgcacg aagaagcagg agctctcgga ggcagagcag gctaccagga   1380
ccatgcaggc tctgccctac agcaccgtgg gcaactccaa caattacctg catctctcag   1440
tgctacgtac agagctcaga cccggggaga ccctcaacgt caacttcctc ctgcgaatgg   1500
accgcgccca cgaggccaag atccgctact acacctacct gatcatgaac aagggcaggc   1560
tgttgaaggc gggacgccag gtgcgagagc ccggccagga cctggtggtg ctgccccctgt   1620
ccatcaccac cgacttcatc ccttccttcc gcctggtggc gtactacacg ctgatcggtg   1680
ccagcggcca gagggaggtg gtggccgact ccgtgtgggt ggacgtcaag gactcctgcg   1740
tgggctcgct ggtggtaaaa agcggccagt cagaagaccg gcagcctgta cctgggcagc   1800
agatgaccct gaagatagag ggtgaccacg ggcccgggt ggtactggtg gccgtggaca   1860
agggcgtgtt cgtgctgaat aagaagaaca aactgacgca gagtaagatc tgggacgtgg   1920
tggagaaggc agacatcggc tgcaccccgg gcagtgggaa ggattacgcc ggtgtcttct   1980
ccgacgcagg gctgaccttc acgagcagca gtggccagca gaccgcccag agggcagaac   2040
```

```
ttcagtgccc gcagccagcc gcccgccgac gccgttccgt gcagctcacg gagaagcgaa    2100
tggacaaagt cggcaagtac cccaaggagc tgcgcaagtg ctgcgaggac ggcatgcggg    2160
agaaccccat gaggttctcg tgccagcgcc ggacccgttt catctccctg ggcgaggcgt    2220
gcaagaaggt cttcctggac tgctgcaact acatcacaga gctgcggcgg cagcacgcgc    2280
gggccagcca cctgggcctg gccaggagta acctggatga ggacatcatt gcagaagaga    2340
acatcgtttc ccgaagtgag ttcccagaga gctggctgtg gaacgttgag gacttgaaag    2400
agccaccgaa aaatggaatc tctacgaagc tcatgaatat attttttgaaa gactccatca    2460
ccacgtggga gattctggct gtgagcatgt cggacaagaa agggatctgt gtggcagacc    2520
ccttcgaggt cacagtaatg caggacttct tcatcgacct gcggctaccc tactctgttg    2580
ttcgaaacga gcaggtggaa atccgagccg ttctctacaa ttaccggcag aaccaagagc    2640
tcaaggtgag ggtggaacta ctccacaatc cagccttctg cagcctggcc accaccaaga    2700
ggcgtcacca gcagaccgta accatccccc ccaagtcctc gttgtccgtt ccatatgtca    2760
tcgtgccgct aaagaccggc ctgcaggaag tggaagtcaa ggctgctgtc taccatcatt    2820
tcatcagtga cggtgtcagg aagtccctga aggtcgtgcc ggaaggaatc agaatgaaca    2880
aaactgtggc tgttcgcacc ctggatccag aacgcctggg ccgtgaagga gtgcagaaag    2940
aggacatccc acctgcagac ctcagtgacc aagtcccgga caccgagtct gagaccagaa    3000
ttctcctgca agggaccccca gtggcccaga tgacagagga tgccgtcgac gcggaacggc    3060
tgaagcacct cattgtgacc ccctcgggct gcggggaaca gaacatgatc ggcatgacgc    3120
ccacggtcat cgctgtgcat tacctggatg aaacggagca gtgggagaag ttcggcctag    3180
agaagcggca gggggccttg gagctcatca agaaggggta cacccagcag ctggccttca    3240
gacaacccag ctctgccttt gcggccttcg tgaaacgggc acccagcacc tggctgaccg    3300
cctacgtggt caaggtcttc tctctggctg tcaacctcat cgccatcgac tcccaagtcc    3360
tctgcggggc tgttaaatgg ctgatcctgg agaagcagaa gcccgacggg gtcttccagg    3420
aggatgcgcc cgtgatacac caagaaatga ttggtggatt acggaacaac aacgagaaag    3480
acatggccct cacggccttt gttctcatct cgctgcagga ggctaaagat atttgcgagg    3540
agcaggtcaa cagcctgcca ggcagcatca ctaaagcagg agacttcctt gaagccaact    3600
acatgaacct acagagatcc tacactgtgg ccattgctgg ctatgctctg cccagatgg    3660
gcaggctgaa ggggcctctt cttaacaaat ttctgaccac agccaaagat aagaaccgct    3720
gggaggaccc tggtaagcag ctctacaacg tggaggccac atcctatgcc ctcttggccc    3780
tactgcagct aaaagacttt gactttgtgc ctcccgtcgt gcgttggctc aatgaacaga    3840
gatactacgg tggtggctat ggctctaccc aggccacctt catggtgttc caagccttgg    3900
ctcaatacca aaaggacgcc cctgaccacc aggaactgaa ccttgatgtg tccctccaac    3960
tgcccagccg cagctccaag atcacccacc gtatccactg gaatctgcc agcctcctgc    4020
gatcagaaga gaccaaggaa aatgagggtt tcacagtcac agctgaagga aaaggccaag    4080
gcaccttgtc ggtggtgaca atgtaccatg ctaaggccaa agatcaactc acctgtaata    4140
aattcgacct caaggtcacc ataaaaccag caccggaaac agaaaagagg cctcaggatg    4200
ccaagaacac tatgatcctt gagatctgta ccaggtaccg gggagaccag gatgccacta    4260
tgtctatatt ggacatatcc atgatgactg ctttgctcc agacacagat gacctgaagc    4320
agctggccaa tggtgttgac agatacatct ccaagtatga gctggacaaa gccttctccg    4380
ataggaacac cctcatcatc tacctggaca aggtctcaca ctctgaggat gactgtctag    4440
```

```
ctttcaaagt tcaccaatac tttaatgtag agcttatcca gcctggagca gtcaaggtct    4500
acgcctatta caacctggag gaaagctgta cccggttcta ccatccggaa aaggaggatg    4560
gaaagctgaa caagctctgc cgtgatgaac tgtgccgctg tgctgaggag aattgcttca    4620
tacaaaagtc ggatgacaag gtcacccctgg aagaacggct ggacaaggcc tgtgagccag    4680
gagtggacta tgtgtacaag acccgactgg tcaaggttca gctgtccaat gactttgacg    4740
agtacatcat ggccattgag cagaccatca agtcaggctc ggatgaggtg caggttggac    4800
agcagcgcac gttcatcagc cccatcaagt gcagagaagc cctgaagctg aggagaaga    4860 aacactacct catgtggggt ctctcctccg atttctgggg agagaagccc aacctcagct    4920
acatcatcgg gaaggacact tgggtggagc actggcccga ggaggacgaa tgccaagacg    4980
aagagaacca gaaacaatgc caggacctcg gcgccttcac cgagagcatg gttgtctttg    5040
ggtgccccaa ctgaccacac ccccattccc ccactccaga taaagcttca gttatatctc    5100
a                                                                     5101
```

<210> SEQ ID NO 2
<211> LENGTH: 1663
<212> TYPE: PRT
<213> ORGANISM: Homo sapiens

<400> SEQUENCE: 2

```
Met Gly Pro Thr Ser Gly Pro Ser Leu Leu Leu Leu Leu Thr His
1               5                   10                  15

Leu Pro Leu Ala Leu Gly Ser Pro Met Tyr Ser Ile Ile Thr Pro Asn
            20                  25                  30

Ile Leu Arg Leu Glu Ser Glu Glu Thr Met Val Leu Glu Ala His Asp
        35                  40                  45

Ala Gln Gly Asp Val Pro Val Thr Val Thr Val His Asp Phe Pro Gly
    50                  55                  60

Lys Lys Leu Val Leu Ser Ser Glu Lys Thr Val Leu Thr Pro Ala Thr
65                  70                  75                  80

Asn His Met Gly Asn Val Thr Phe Thr Ile Pro Ala Asn Arg Glu Phe
                85                  90                  95

Lys Ser Glu Lys Gly Arg Asn Lys Phe Val Thr Val Gln Ala Thr Phe
            100                 105                 110

Gly Thr Gln Val Val Glu Lys Val Val Leu Val Ser Leu Gln Ser Gly
        115                 120                 125

Tyr Leu Phe Ile Gln Thr Asp Lys Thr Ile Tyr Thr Pro Gly Ser Thr
    130                 135                 140

Val Leu Tyr Arg Ile Phe Thr Val Asn His Lys Leu Leu Pro Val Gly
145                 150                 155                 160

Arg Thr Val Met Val Asn Ile Glu Asn Pro Glu Gly Ile Pro Val Lys
                165                 170                 175

Gln Asp Ser Leu Ser Ser Gln Asn Gln Leu Gly Val Leu Pro Leu Ser
            180                 185                 190

Trp Asp Ile Pro Glu Leu Val Asn Met Gly Gln Trp Lys Ile Arg Ala
        195                 200                 205

Tyr Tyr Glu Asn Ser Pro Gln Gln Val Phe Ser Thr Glu Phe Glu Val
    210                 215                 220

Lys Glu Tyr Val Leu Pro Ser Phe Glu Val Ile Val Glu Pro Thr Glu
225                 230                 235                 240

Lys Phe Tyr Tyr Ile Tyr Asn Glu Lys Gly Leu Glu Val Thr Ile Thr
                245                 250                 255
```

-continued

```
Ala Arg Phe Leu Tyr Gly Lys Lys Val Glu Gly Thr Ala Phe Val Ile
            260                 265                 270

Phe Gly Ile Gln Asp Gly Glu Gln Arg Ile Ser Leu Pro Glu Ser Leu
        275                 280                 285

Lys Arg Ile Pro Ile Glu Asp Gly Ser Gly Glu Val Val Leu Ser Arg
    290                 295                 300

Lys Val Leu Leu Asp Gly Val Gln Asn Pro Arg Ala Glu Asp Leu Val
305                 310                 315                 320

Gly Lys Ser Leu Tyr Val Ser Ala Thr Val Ile Leu His Ser Gly Ser
                325                 330                 335

Asp Met Val Gln Ala Glu Arg Ser Gly Ile Pro Ile Val Thr Ser Pro
            340                 345                 350

Tyr Gln Ile His Phe Thr Lys Thr Pro Lys Tyr Phe Lys Pro Gly Met
        355                 360                 365

Pro Phe Asp Leu Met Val Phe Val Thr Asn Pro Asp Gly Ser Pro Ala
    370                 375                 380

Tyr Arg Val Pro Val Ala Val Gln Gly Glu Asp Thr Val Gln Ser Leu
385                 390                 395                 400

Thr Gln Gly Asp Gly Val Ala Lys Leu Ser Ile Asn Thr His Pro Ser
                405                 410                 415

Gln Lys Pro Leu Ser Ile Thr Val Arg Thr Lys Lys Gln Glu Leu Ser
            420                 425                 430

Glu Ala Glu Gln Ala Thr Arg Thr Met Gln Ala Leu Pro Tyr Ser Thr
        435                 440                 445

Val Gly Asn Ser Asn Asn Tyr Leu His Leu Ser Val Leu Arg Thr Glu
    450                 455                 460

Leu Arg Pro Gly Glu Thr Leu Asn Val Asn Phe Leu Leu Arg Met Asp
465                 470                 475                 480

Arg Ala His Glu Ala Lys Ile Arg Tyr Tyr Thr Tyr Leu Ile Met Asn
                485                 490                 495

Lys Gly Arg Leu Leu Lys Ala Gly Arg Gln Val Arg Glu Pro Gly Gln
            500                 505                 510

Asp Leu Val Val Leu Pro Leu Ser Ile Thr Thr Asp Phe Ile Pro Ser
        515                 520                 525

Phe Arg Leu Val Ala Tyr Tyr Thr Leu Ile Gly Ala Ser Gly Gln Arg
    530                 535                 540

Glu Val Val Ala Asp Ser Val Trp Val Asp Val Lys Asp Ser Cys Val
545                 550                 555                 560

Gly Ser Leu Val Val Lys Ser Gly Gln Ser Glu Asp Arg Gln Pro Val
                565                 570                 575

Pro Gly Gln Gln Met Thr Leu Lys Ile Glu Gly Asp His Gly Ala Arg
            580                 585                 590

Val Val Leu Val Ala Val Asp Lys Gly Val Phe Val Leu Asn Lys Lys
        595                 600                 605

Asn Lys Leu Thr Gln Ser Lys Ile Trp Asp Val Val Glu Lys Ala Asp
    610                 615                 620

Ile Gly Cys Thr Pro Gly Ser Gly Lys Asp Tyr Ala Gly Val Phe Ser
625                 630                 635                 640

Asp Ala Gly Leu Thr Phe Thr Ser Ser Ser Gly Gln Gln Thr Ala Gln
                645                 650                 655

Arg Ala Glu Leu Gln Cys Pro Gln Pro Ala Ala Arg Arg Arg Arg Ser
            660                 665                 670

Val Gln Leu Thr Glu Lys Arg Met Asp Lys Val Gly Lys Tyr Pro Lys
        675                 680                 685
```

```
Glu Leu Arg Lys Cys Cys Glu Asp Gly Met Arg Glu Asn Pro Met Arg
    690             695                 700
Phe Ser Cys Gln Arg Arg Thr Arg Phe Ile Ser Leu Gly Glu Ala Cys
705             710                 715                 720
Lys Lys Val Phe Leu Asp Cys Cys Asn Tyr Ile Thr Glu Leu Arg Arg
            725                 730                 735
Gln His Ala Arg Ala Ser His Leu Gly Leu Ala Arg Ser Asn Leu Asp
        740                 745                 750
Glu Asp Ile Ile Ala Glu Asn Ile Val Ser Arg Ser Glu Phe Pro
    755                 760                 765
Glu Ser Trp Leu Trp Asn Val Glu Asp Leu Lys Glu Pro Pro Lys Asn
770             775                 780
Gly Ile Ser Thr Lys Leu Met Asn Ile Phe Leu Lys Asp Ser Ile Thr
785             790                 795                 800
Thr Trp Glu Ile Leu Ala Val Ser Met Ser Asp Lys Lys Gly Ile Cys
                805                 810                 815
Val Ala Asp Pro Phe Glu Val Thr Val Met Gln Asp Phe Phe Ile Asp
            820                 825                 830
Leu Arg Leu Pro Tyr Ser Val Arg Asn Glu Gln Val Glu Ile Arg
        835                 840                 845
Ala Val Leu Tyr Asn Tyr Arg Gln Asn Gln Glu Leu Lys Val Arg Val
850                 855                 860
Glu Leu Leu His Asn Pro Ala Phe Cys Ser Leu Ala Thr Thr Lys Arg
865                 870                 875                 880
Arg His Gln Gln Thr Val Thr Ile Pro Pro Lys Ser Ser Leu Ser Val
                885                 890                 895
Pro Tyr Val Ile Val Pro Leu Lys Thr Gly Leu Gln Glu Val Glu Val
            900                 905                 910
Lys Ala Ala Val Tyr His His Phe Ile Ser Asp Gly Val Arg Lys Ser
        915                 920                 925
Leu Lys Val Val Pro Glu Gly Ile Arg Met Asn Lys Thr Val Ala Val
    930                 935                 940
Arg Thr Leu Asp Pro Glu Arg Leu Gly Arg Glu Gly Val Gln Lys Glu
945                 950                 955                 960
Asp Ile Pro Pro Ala Asp Leu Ser Asp Gln Val Pro Asp Thr Glu Ser
                965                 970                 975
Glu Thr Arg Ile Leu Leu Gln Gly Thr Pro Val Ala Gln Met Thr Glu
            980                 985                 990
Asp Ala Val Asp Ala Glu Arg Leu Lys His Leu Ile Val Thr Pro Ser
        995                 1000                1005
Gly Cys Gly Glu Gln Asn Met Ile Gly Met Thr Pro Thr Val Ile
    1010            1015                1020
Ala Val His Tyr Leu Asp Glu Thr Glu Gln Trp Glu Lys Phe Gly
    1025            1030                1035
Leu Glu Lys Arg Gln Gly Ala Leu Glu Leu Ile Lys Lys Gly Tyr
    1040            1045                1050
Thr Gln Gln Leu Ala Phe Arg Gln Pro Ser Ser Ala Phe Ala Ala
    1055            1060                1065
Phe Val Lys Arg Ala Pro Ser Thr Trp Leu Thr Ala Tyr Val Val
    1070            1075                1080
Lys Val Phe Ser Leu Ala Val Asn Leu Ile Ala Ile Asp Ser Gln
    1085            1090                1095
Val Leu Cys Gly Ala Val Lys Trp Leu Ile Leu Glu Lys Gln Lys
```

-continued

```
            1100              1105              1110

Pro Asp Gly Val Phe Gln Glu Asp Ala Pro Val Ile His Gln Glu
    1115              1120              1125

Met Ile Gly Gly Leu Arg Asn Asn Asn Glu Lys Asp Met Ala Leu
    1130              1135              1140

Thr Ala Phe Val Leu Ile Ser Leu Gln Glu Ala Lys Asp Ile Cys
    1145              1150              1155

Glu Glu Gln Val Asn Ser Leu Pro Gly Ser Ile Thr Lys Ala Gly
    1160              1165              1170

Asp Phe Leu Glu Ala Asn Tyr Met Asn Leu Gln Arg Ser Tyr Thr
    1175              1180              1185

Val Ala Ile Ala Gly Tyr Ala Leu Ala Gln Met Gly Arg Leu Lys
    1190              1195              1200

Gly Pro Leu Leu Asn Lys Phe Leu Thr Thr Ala Lys Asp Lys Asn
    1205              1210              1215

Arg Trp Glu Asp Pro Gly Lys Gln Leu Tyr Asn Val Glu Ala Thr
    1220              1225              1230

Ser Tyr Ala Leu Leu Ala Leu Leu Gln Leu Lys Asp Phe Asp Phe
    1235              1240              1245

Val Pro Pro Val Val Arg Trp Leu Asn Glu Gln Arg Tyr Tyr Gly
    1250              1255              1260

Gly Gly Tyr Gly Ser Thr Gln Ala Thr Phe Met Val Phe Gln Ala
    1265              1270              1275

Leu Ala Gln Tyr Gln Lys Asp Ala Pro Asp His Gln Glu Leu Asn
    1280              1285              1290

Leu Asp Val Ser Leu Gln Leu Pro Ser Arg Ser Ser Lys Ile Thr
    1295              1300              1305

His Arg Ile His Trp Glu Ser Ala Ser Leu Leu Arg Ser Glu Glu
    1310              1315              1320

Thr Lys Glu Asn Glu Gly Phe Thr Val Thr Ala Glu Gly Lys Gly
    1325              1330              1335

Gln Gly Thr Leu Ser Val Val Thr Met Tyr His Ala Lys Ala Lys
    1340              1345              1350

Asp Gln Leu Thr Cys Asn Lys Phe Asp Leu Lys Val Thr Ile Lys
    1355              1360              1365

Pro Ala Pro Glu Thr Glu Lys Arg Pro Gln Asp Ala Lys Asn Thr
    1370              1375              1380

Met Ile Leu Glu Ile Cys Thr Arg Tyr Arg Gly Asp Gln Asp Ala
    1385              1390              1395

Thr Met Ser Ile Leu Asp Ile Ser Met Met Thr Gly Phe Ala Pro
    1400              1405              1410

Asp Thr Asp Asp Leu Lys Gln Leu Ala Asn Gly Val Asp Arg Tyr
    1415              1420              1425

Ile Ser Lys Tyr Glu Leu Asp Lys Ala Phe Ser Asp Arg Asn Thr
    1430              1435              1440

Leu Ile Ile Tyr Leu Asp Lys Val Ser His Ser Glu Asp Asp Cys
    1445              1450              1455

Leu Ala Phe Lys Val His Gln Tyr Phe Asn Val Glu Leu Ile Gln
    1460              1465              1470

Pro Gly Ala Val Lys Val Tyr Ala Tyr Tyr Asn Leu Glu Glu Ser
    1475              1480              1485

Cys Thr Arg Phe Tyr His Pro Glu Lys Glu Asp Gly Lys Leu Asn
    1490              1495              1500
```

```
Lys Leu Cys Arg Asp Glu Leu Cys Arg Cys Ala Glu Glu Asn Cys
1505                1510                1515

Phe Ile Gln Lys Ser Asp Asp Lys Val Thr Leu Glu Glu Arg Leu
1520                1525                1530

Asp Lys Ala Cys Glu Pro Gly Val Asp Tyr Val Tyr Lys Thr Arg
1535                1540                1545

Leu Val Lys Val Gln Leu Ser Asn Asp Phe Asp Glu Tyr Ile Met
1550                1555                1560

Ala Ile Glu Gln Thr Ile Lys Ser Gly Ser Asp Glu Val Gln Val
1565                1570                1575

Gly Gln Gln Arg Thr Phe Ile Ser Pro Ile Lys Cys Arg Glu Ala
1580                1585                1590

Leu Lys Leu Glu Glu Lys Lys His Tyr Leu Met Trp Gly Leu Ser
1595                1600                1605

Ser Asp Phe Trp Gly Glu Lys Pro Asn Leu Ser Tyr Ile Ile Gly
1610                1615                1620

Lys Asp Thr Trp Val Glu His Trp Pro Glu Glu Asp Glu Cys Gln
1625                1630                1635

Asp Glu Glu Asn Gln Lys Gln Cys Gln Asp Leu Gly Ala Phe Thr
1640                1645                1650

Glu Ser Met Val Val Phe Gly Cys Pro Asn
1655                1660

<210> SEQ ID NO 3
<211> LENGTH: 42783
<212> TYPE: DNA
<213> ORGANISM: Homo sapiens

<400> SEQUENCE: 3
ctcctcccca tcctctccct ctgtccctct gtccctctga ccctgcactg tcccagcacc      60
atgggaccca cctcaggtcc cagcctgctg ctcctgctac taacccacct ccccctggct     120
ctggggagtc ccatgtgagt ggttatgact ctacccacaa acagggctgg ttctggggtg     180
gaagcagaca tttgggggtc caggtccctg tagaattcag ggtgcatttg ggtgtttgtg     240
gattcagggg ttagcaggtt gggaatgatt atatatattt gggctgcctg tgagtttggg     300
tgtttgtggt tgggtgtttg tggaatccag gtatcatgga attggagttt atatacattt     360
gggctgcctg tgagtttggg tgtttgtggt tgggtgtttg tggaatccag gtatcgtgga     420
attggagttt atatacattt gggctgcctg agagtttggg tgtttatggg ttgggtgttt     480
gtggaatcca ggtatggtgg aattggagtt tgggatgttt ctagaattga ggtcatctgt     540
tggtttaggg tgtatgtggt gttcattgat ggtgcggttg ggggtgtttg gagactcgga     600
ggtttggact ttacaagatt tgggagtttg cagcttgggg acttgcaatt ttcagtgtgg     660
gtttaaagat tggctacttc gggttcatgt atagttgggg catttggaat tgattgtatt     720
tattaggact ggggtgttgg aggtttaggc tgggtttggg gtgctctaag atttgaggtt     780
tagaggtttt ggcgtatgtg ggtttgggta ggtagagttg agggtgtccg ggagtttgag     840
tgtttacata tttggagtgt ttagagaggt agaggtttag ggtttggggc atgtgtgggt     900
ttaggcgatt gtgggtctgg aagtccagag acttggagga gttgctgacg ctggttggaa     960
ggttcagggt ttggtgggat gtgtggcccc ctcgttgccc aggcttttcaa aggccaggcc    1020 cagctggctg agagtgggag tcatggtggc tgctgtcctg cccatgtggt tgagacggtg    1080
gcagtgccca gagaagataa tggcattggc aagtgcgccg gcagtcactg gatcctctcc    1140
aggaccagag gctggggcac acagcctgcc aggcgctgac tccagtgagg actggcgtct    1200
```

```
cacatccgtg gaatgacaag cccactcccg tgccccactc cgacaggtac tctatcatca   1260
cccccaacat cttgcggctg gagagcgagg agaccatggt gctggaggcc cacgacgcgc   1320
aaggggatgt tccagtcact gttactgtcc acgacttccc aggcaaaaaa ctagtgctgt   1380
ccagtgagaa gactgtgctg accccctgcca ccaaccacat gggcaacgtc accttcacgg   1440
tgagtgcaga ctggcgcagg acccggctga cacccacagc cacgcccact ccccccctcc   1500
tcctgagccc ctcccttct gtcttctccc tttctaagcc ctgcccttcc ctgagactcc   1560
accccttcgg agtcgcctct ccttctaagc ccctcccttc tctgagactc caccccttct   1620
gagtctcctc cccttataag cccctccctt ttctgagacc ccccccacc ccttctgaat   1680 ctcctcccct tctaagccct gaccttccct gagaccccac cccttctgag actcctcccc   1740
ttctgagtcc ctcccttccc tgagacccca cccttctga ggttcctccc cttctctgag   1800
actccacccc ttctgagtct cctcccctc taagtccctc ccactgaatt cctttccaa    1860 gcccctcccc ctcgaagtct cctcttctga actcctcccc tcttagtctc catcactttc   1920
taagttccct cacctgagtc cctcccctt tctgagcccc tcccatgtca gcccttccc    1980 tttctgagtc cccgccccctt ctgagcccct cctcctataa gctctctcct ccttgtgagc   2040
tcttcttttt gagttccctc cctggtcccc cctctcccct cgcacctcct tcacatgccc   2100
ctccctcccc aaaacggcca cctcggaaga ccaagaataa tgggcaggca aggagggacc   2160
cagcccaaga tccggaagct ggaccgtggg catggggcct ggaacagac ccctgacaat   2220 gccctgccca cgcctagatc ccagccaaca gggagttcaa gtcagaaaag gggcgcaaca   2280
agttcgtgac cgtgcaggcc accttcggga cccaagtggt ggagaaggtg gtgctggtca   2340
gcctgcagag cggtacctc ttcatccaga cagacaagac catctacacc cctggctcca   2400
caggtgaggc tgggggcggc tggagagggc ggggcaccgg cgtgggcggg ctagggtctc   2460
acgaggcctc tttgtctctc cccagttctc tatcggatct tcaccgtcaa ccacaagctg   2520
ctacccgtgg gccggacggt catggtcaac attgaggtgc agccagagg gggccccagg   2580 ggaagcaggg gcacaggctt aggagaggca aagagatcga gagagacaga gaaagacaca   2640
ccggaagggg tgcagtggca gagacacaga ggcaaagaga tatgcagaca cacccaca    2700 caacacacac acatacagca cacaacatgc acacacacag cacaaatac acacacagag   2760 gcaaagagat atgcagacac atgtgcacac acaatgcaca cacacaatgc aacacacaca   2820
aacacacaac atacacgacc acacaacaca cacaacacaa cacaacacac aatacacaca   2880
gcacaacgtg catgaccaca cacacaacac acaacacaca caacacaata cacaacatac   2940
acaaccacgc aatacacaca aaacacacac aacacaacac aacatacata accacaccac   3000
acacaacaca caaccacaca cactatcac acaacacaca caaacacaca caacacacaa   3060
cacacacaac acacacaaaa cacaacacac acacaacata cacaaccaca caacacacaa   3120
ccacacaaca tacacgacca cacaacacag tgcacacaaa catagcacac acaacacaca   3180
acccaacaca caaccacaca atacaccata tggcgcgcac acacacacac acacacacac   3240
aggctgagag acaaggtgga gatccaggga gaccccaggg agcagtgcag gtgtccgtgg   3300
attctgcttt cagttaaacc cctgatcact tcacctccct gagcctcagt taccttatct   3360
gaatatcggg atcatgacgg ataattgtat gtcatctatt ctaccgacgg cagccagagg   3420
acgcctgtga gcacctgagt cagggcccat ccctgctctg cctacagccc tccatggctc   3480
ccaccttcct atgcgtcaaa gcccaagtcc tccctgcagt ccacaaggcc ctgcacacct   3540
tgccctgtcc cttccctgcc ctcccctcct ccctctctcc ccctcgttca ctcttctgga   3600
```

```
gccacacggg ccatcctccc tgttcctcca acacccaggt gcagtcctgc cttggcgcct    3660
tggcacgggc tgtgccctct tctcaagaaa accctcttct tccaaatatc cacacagctt    3720
gttctctctc ctcctttaag tctttgctca aatgtcacca atgtctcaat tttacaatga    3780
ggtctctctg agtaacctat aaagtcgcaa atacccaccc tgagcgtccc ccctccccgc    3840
tacacacact cctccttcct gccatgtcct gcaaatgaga tttattcatt tgataattgc    3900
ttctcccatc gcctcgccct ctattgaacc taaatccctc caggaaggaa ttgttatgtt    3960
tgttgagggt tttgtcacct gaactcagca caatgctggt atatagttgg gtttaataaa    4020
aaacttactg gaagaagcga gaaggatggg aggagagaag gggaaggagg gtgttctcat    4080
agaattatca tgaggatgtg ttgaaatcat acaaggctag gtgcagtggc tcacacttgt    4140
aatcccagct gtttgggagg ccaaggcggg aggatcgctt gagcccaaga gtccaagacc    4200
agcctgggca acacagccag accctgtctc tacaaaaaag aaaagttaaa aacaaacaaa    4260
aaaacagctg tgtgtggtgg tgcttgcttg tggttgcagc tacccagga ggctgaggca    4320 ggaggatcac ttgagcccag gaattccagg ctgcagtgag ccgtgatcgc accactgcac    4380
tccagcctgg gtggcagagt gagaccctgt ctcaaaaaat aattgggca aatgcaatgg    4440 ctcaagcctg taattccaac atttcgggag gcagaggtgg gaagactgct cgaggccaag    4500
agttcaagac cagcctggga aagctaggga gactacatct ctacaaaaaa aatgtaaaaa    4560
ttatctagat ttagggattg atgtggtctg tggggaacag agaccacaca tctcttgtaa    4620
aggcacaaca gttgcccagc tccaattaga tgtctcctgc taaccagagt acactatcca    4680
cagaaatttc cttgtttcca acagaagcta gaaaaacaga ttttggcca ggtgcagtgg    4740 ctcactccta taatcccagc actttgggag gtggaggcgg gcagatcacg aggtcaggag    4800
atcgagacca tcctggctaa cacggtgaaa ccccgtcttt attaaaagta caaaaaaaaa    4860
attagctggg cgtggtggcg ggcacctgta gtcccagcta ctcgagaggc tgaggcagga    4920
gaatggtgtg aacccgggag gcggagcctg cagtgagccg agatctcgcc attacactcc    4980
agcctgggcg acagagcaag actccgtctc aaaaaaaaaa acaaaaaaaa caaaaaaaaa    5040
acagattttt atatgtttta attcctaaag ccagctcacg gccttcagat atgccacttg    5100
cctgatccct gttacctctg tacaatttct tttaaactta tttattcatt cattcattca    5160
ttattattat ttttgagaca gggtctcatt ctgttgccca ggctagagtg cagtggcaca    5220
atcacagctc actgcagcat tgacctcctg ggcccaagct gtcctcctgt ctcagcctcc    5280
tgggtagctg ggaccacaga cgtgcgccac cacatccagc taatttttaaa aaattttttgt    5340 agagatggag tctcccctaca ttttcccaggc tggtcttgaa cccttgacct tgagcaatct    5400
tcccacttct gcctctcaaa gtgctgggat tacaggcttg agccattgcg ctcgccctaa    5460
tacattattt tttgagatgg ggtctcgctc tttcacccag actggagtgc agtggtgcaa    5520
tgatgtctca tgatgtttaa atgttggcag caaatgaaat gacactacta gttattagta    5580
ttcagagaga cactgaaaaa atgagcccct actcatatga actatgtccc aagccaacac    5640
agtaggtgcc attataatct cctgtttcaa gatttgcaca ttgagcacag agaggttagg    5700
taacttgccc agggtcacac agcttgtaag tggcacagta gagattgaaa cctaaggttg    5760
actgactccg gtccttgttc tttttttcga gacagactct cactctgtct cccaggctgg    5820
agtgcagtgg agtgatcttg gctctctgca atctccgcct cccggggttca agcgattctc    5880 ccgcctcagc ctcctgagta gctgggatta cgggtgccta ccaccatgcc tggctaattt    5940
ttgtattttt agtagagaca gggtttcatc acgttggcca ggctggtctt gaactcctga    6000
```

```
cctcaggtga tctgcccgcc tcagcctccc agagtgctgg gatgacaggc gtgagccgct   6060
gcgcccacct gggtccctgt tcttaaccac agtagacact gtgcacagag aatgtccaga   6120
cacaggtcgg ggagagctga gaggctaagc ccagcctccg aagagccact ttatcctcta   6180
tccttccctc ctgcctccca cagaacccgg aaggcatccc ggtcaagcag gactccttgt   6240
cttctcagaa ccagcttggc gtcttgccct tgtcttggga cattccggaa ctcgtcaagt   6300
atgtcaggtt cttgaggagg gggctcaggg ctcccctatc cccggagagg gagcagggg    6360 gctccgaggc ctgagagacc actcatccgc cctcctcaca gcatgggcca gtggaagatc   6420
cgagcctact atgaaaactc accacagcag gtcttctcca ctgagtttga ggtgaaggag   6480
tacggtaaga ggaggagggg ctgggggag tcagtgccca gaacgcctgg cccagcgccg    6540
gccccaccaa cgccatctct cccccagtgc tgcccagttt cgaggtcata gtggagccta   6600
cagagaaatt ctactacatc tataacgaga agggcctgga ggtcaccatc accgccaggt   6660
gagggactgg gggtggggcc aggtaagagc caggtgaggg accaggtgaa gaccaggtgg   6720
gggactgggg gtggagtcag gtgggggct  ggagatggga ccaggtgggg gctgggggt    6780 ggagtcaggt gggggctgg  gggtggggaa ggtggggggc tggggtggg  gcaaggtgag   6840 gggctggggg tggaccagg  tgggggctg  ggggtggag  tcaggtgggg gctgggagtg   6900
gggaaggtgg ggggctgggg gtgggccag  gtgaggggct ggaggtggga ccatgtgggg   6960
ggtgggagtg gggcaaggtg gggggctggg ggtgggccca ggtgaggggc tggaggtggg   7020
gccaggtgag aggccagcag tgggttgggg gctccagtct tcagcacagg caggagaagc   7080
tgggggagat cccattctcc aggagggatg gacctgaagc cctccttgtc tgtcccgtag   7140
gttcctctac gggaagaaag tggagggaac tgcctttgtc atcttcggga tccaggatgg   7200
cgaacagagg atttccctgc ctgaatccct caagcgcatt ccggtaccat agacggaggc   7260
cgctttgatc cctgccccag tccccgccac ctctgagccc gctccctct  ctgagccctc   7320 ctctccttc  tcagattgag gatggctcgg gggaggttgt gctgagccgg aaggtactgc   7380 tggacgggt  gcagaacccc cgagcagaag acctggtggg gaagtctttg tacgtgtctg   7440
ccaccgtcat cttgcactca ggtgaggccc agtctgaagg ccaggctcag gaccaccaag   7500
tgggccggtc tgagagggga gaccaggtca aagagaaag  cctagtctaa ggagggaggc   7560
tcagagtgaa agtggggttc agtctgatgg ggtaggccca gtctgagagg ggaggccgag   7620
tatgaagatg gattccagcc tgatggggg  aggcagggcc agtataaagg tggggtccgg   7680
gctgatgggg gcacaggccc agtatgaagt ctgtgtccag tctgatgagg gaggcagggc   7740
cagtataaag atgggtccag tctgatgggg gaggcagggc cagtataaag gtggggtccg   7800
gtctgatggg ggtcacaggc ccagtatgaa gtctgtgcca gtctgatgga ggaggcaagg   7860
ccagtataaa ggtggagtcc agtctgatgg ggggcacagg cccagtatga agtggactc    7920 tactctgagg gaggaggtct agtctgaagt tgggtccat  tctgagggag gaggtctaat   7980 cctgagggt  ggcccagaag cctacactca cagctggtcc cctcaggcag tgacatggtg   8040
caggcagagc gcagcgggat ccccatcgtg acctctccct accagatcca cttccccaag   8100
acacccaagt acttcaaacc aggaatgccc tttgacctca tggtgagacc cggggcggga   8160
aggggtccca ctcctccctt cggggacacc ggccacagcc ctgagcctgc ctgaacttcc   8220
cccacctgca ccccacatca caggtgttcg tgacgaaccc tgatggctct ccagcctacc   8280
gagtccccgt ggcagtccag ggcgaggaca ctgtgcagtc tctaacccag ggagatggcg   8340 tggccaaaact cagcatcaac acacaccccc agccagaagcc cttgagcatc acggtgcgtc   8400
```

```
tgggcccagc ctcggaaccc catcactggg aagacggtac aggggttctg gtgtttgcac    8460
agtggggtcc tgtcatttgc atacagatat tctcatctgc atagagaggt tctctcctgc    8520
gcagagggt  cctgccattt gcatagagat actctcatct gcatagaggg gttctgtcct    8580
gcacagtggg gtcctgccat ttgcatagac attctcattt gcctagaggg gttctgtcct    8640
gcacagtggg gtcctgccgt ctgcatggag gggtccgcag tttgaggaaa caggaatctt    8700
cctcttgcat gccctgctcc ttccacttac acggagaggc gctccatcca cgcacagtct    8760
ttccactccc atgggggaag gagcctgaat ctcacaagga gggttgtgta gtgtttggga    8820
caggcccatt gttgtgaggt ggtctcagtt ctcctggctt ctgtgcacgt ggctctgttg    8880
cccctcactg ggagggaagc aagtctcatg acagctgcgg aggttgcaga tggcctccca    8940
gtccctctgc agctcccagg ctgcgcaccc cacttacccc tccctgtgct cagcatgtgc    9000
gtgaatttcc ggtggctacc atgagaaatg gccacagcct agtgatctaa agcaacacac    9060
atttatgggt ctatagtttg agaggtcaga agtcctggct ctgggggaaa gttcgctccc    9120
ttgcttttc  cagtgtcgcc agggcaccct aaaggcctgg ctcatggccc cttcctccac    9180
cttaaaggc  agcagcatag catcttccag tgtctctctt tctctctgtc tctgtctctc    9240
ctttctcccc tgcccctgct aataaagac  ccttatgatt acattagctc cacctacata    9300
atccaggata atgattccat ctccagatcc ctaacttaat cccatctgca aagccccttt    9360
tgttaagaaa ggccaccaat tcccaggtct cagggattcg ggtgtgggta tcctcgggcg    9420
gcgaccagca ggcatccctc tttccccacc caggtgcgca cgaagaagca ggagctctcg    9480
gaggcagagc aggctaccag gaccatgcag gctctgccct acagcaccgt gggcaactcc    9540
aacaattacc tgcatctctc agtgctacgt acagagctca gacccgggga gaccctcaac    9600
gtcaacttcc tcctgcgaat ggaccgcgcc cacgaggcca agatccgcta ctacacctac    9660
ctggtccgtg gccacctgga aacctcagcc cccgcctcct ccttgtttct tccgcacccc    9720
tgggactcct tcccccatcc cggatccctc cctgcgttcc ctgccactca ccctccccag    9780
cctgatgcca gcctgtcccc ccagatcatg aacaagggca ggctgttgaa ggcgggacgc    9840
caggtgcgag agcccggcca ggacctggtg gtgctgcccc tgtccatcac caccgacttc    9900
atcccttcct tccgcctggt ggcgtactac acgctgatcg gtgccagcgg ccagagggag    9960
gtggtggccg actccgtgtg ggtggacgtc aaggactcct gcgtgggctc ggtaagtgtg   10020
ccctgggctc gctcgccccc tctccctctc cctactcctc tctctctctc tctctccctg   10080
tctcctctct ctctctctct cccttttctcc ttttctctct cctttctctc tcttctcttc   10140
ctctcccttt ctctcctccc tctctgtctc tcaactgtct ctcttttat  ctctctttcc   10200
ctctctctac atctctcttt ccctctctct ttatttctct ttccttctct ctctccctct   10260
ctcgatctct ctttctctcc atctctctcc ttttctctct ccctctctct ctccttttct   10320
ctctccctgt ctctttccct ttccctctct ctccctctct tttctctccc tctctctttc   10380
cctctccctc tctctctccc tttctctctc tccctctctc tccttctctc tccctctttc   10440
tctccttctc tctttccctc tctctctccc tctctctttc cctctctctc cctctcccttt  10500
tctctccctc tttcccttc  cctctctccc ccctcactct ccctctctct gtctctccgt   10560
ctctctccct ctctccctgt ctctccgtct ctctccctgt ctctcccttt ctctctctct   10620
cccgccctct ctccctctct ctccctccct ctctcccttt ctctctctct ccctctctct   10680
cccctcccc  agcccacgg  ctccccccaa cctttctgtc tttccactct agcccagcac   10740
ccactccatc ccaggcactc ctctctccca gggctgactt ctttcggcgt ctccaccctc   10800
```

```
cccacagctg gtggtaaaaa gcggccagtc agaagaccgg cagcctgtac ctgggcagca   10860
gatgaccctg aagatagagg gtgaccacgg ggcccgggtg gtactggtgg ccgtggacaa   10920
gggcgtgttc gtgctgaata agaagaacaa actgacgcag agtaaggtaa gggccagtga   10980
cccaaggctg ctgagaagag gcggaggcac ggagctgggg ctgggggagg tgggtgggac   11040
tggagagggc agtgcagtgg ggggcatgcg ctgaaagcag agatcggagc agaccagaca   11100
cagggatggt tgaagctgaa gatgggaatg aggttggaca tgggttccaa ttggggatgg   11160
tcctgagaat tggactttt tttctgtttg tttgtttgtt tttgagacag agtctctctc    11220
tgtcaccagg ctggagtgca gtggcacaat ctcggctcac tgcaacctct gcctcccagg   11280
ttcaagcgat tctcctgcct cagcttccct agtagctggg actacaggtg cccatcacca   11340
cgcccagcta atttttgtat ttttagtgaa gacgggggtt tcaccatgtt ggccaggatg   11400
gtctcgatct cttggccttg tgatccaccc gcctcgacct cccaaagtgt tgggattaca   11460
ggcgtgagcc actgcgcccg gctgagaatt ggacactttc aactgggggcc ctgagaggct   11520 ggtggcagca cacccagggt cattcagtgg ggaaggtttc cggagtaggg acgaagatgg   11580
agatggggtt ggcttgggat caggagtgag gatgggaatg cagatggaat cagaggggaa   11640
atggagataa gatttggaat ggaggccagg tgcggtggct cacgtctgga atcccagcac   11700
tttgggaggt caaggtggga ggatcacttg aggccaggag ttcagaccag cttgggcaac   11760
atggcaagac cccatctcta cagaaaaaat tttaaaatag ctgggcatga tggcgcatgc   11820
ctgtagtccc atctgctcag gaggcagagg tgcgaggatt gcttgagccc aggaatttga   11880
ggctgcagtg agctatgcct gcaccactgc actccagcct gggagacagt ggaaaatccc   11940
aacttaaaaa aaaaaaaaaa gaatggaaag aaaggaggaa aaaaaagaa gagagagaga    12000 aacagagaga aagaaaaaga aaggagataa agaggaaggg agggagggag tgaagaatga   12060
aggaaggaaa gaaggaagga aggaaggagg gaaggaggga aggaaggggg gagcaaagga   12120
aggaggaaag gaggaatgga gggaggaagg gagggagagg aaggaaggga aagaaagaag   12180
acagaaagaa aagaaaaaga aggccgggca tggtggctca ctcctgtaat cccttttggga   12240 ggccaagcac tttgggaggc caagacaggc gaatcatttc aggtcaggag ttcgagacca   12300
gcctggccaa catggtgaaa tcccgtctct actaaatata taaaaattag ctgggcatgg   12360
tggcatgcac ctgtagtccc agatactcgg gaggctgagg caggaaaatt gcctgaacct   12420
gggagttgga ggttacagtg agcggagatc acaccactgc actccagcct gggtgacaga   12480
gcaagactcc atctcgaaag aaagaaagag agagagtgag aaagagaaag aaaaagagaa   12540
ggaaggagag agaaggaagg aaggaaagag aaagagaaag gaagggcaga agcaggaatg   12600
ggggagatga gagtgggaca gggtgggtc atttgggaag agatacacag gtgcatatgt    12660 ggggggatccc aattgtcagc ctggcctccc tgcgtcccgc cacccctatg ccccccgcag   12720
atctgggacg tggtggagaa ggcagacatc ggctgcaccc cgggcagtgg gaaggattac   12780
gccggtgtct tctccgacgc agggctgacc ttcacgagca gcagtggcca gcagaccgcc   12840
cagagggcag gtgaggtcgc caccaggggc cggtgcaggg acagacagca cctccacctc   12900
ccagatgctg ggagcagagc tctgaaaacc ggggcctgg gttcaagccc cgcctccacc    12960
accacctagt aaatccctcc cctctgagcc tcagtttgct cttccatcaa atgggagcag   13020
gaacaccccc acctcacacg atcgtgaggg gtgaaccgag gacacctagt aggtgcctca   13080
tccatcttct tctcggtccg cctgccctgc agaacttcag tgcccgcagc cagccgcccg   13140
ccgacgccgt tccgtgcagc tcacggagaa gcgaatggac aaaggtggga gcctttccta   13200
```

```
cccactcctg cccccgagcc caccccagg  agacccagc  ccggccgtgc aggagccaga 13260
gagggaggag gggaggccct ggcggcgggg aagtcctccc tggggtccgt cccgcgtccc 13320
tcctgctgcc ggcccccggc tgagggtgtg gcctggggga acacgtgctc ccgcagtcgg 13380
caagtacccc aaggagctgc gcaagtgctg cgaggacggc atgcgggaga accccatgag 13440
gttctcgtgc cagcgccgga cccgtttcat ctccctgggc gaggcgtgca agaaggtctt 13500
cctggactgc tgcaactaca tcacagagct gcggcggcag cacgcgcggg ccagccacct 13560
gggcctggcc aggagtaggt cccacggggt gggacaggg  ggaggggcc  gtctgatggg 13620
ggaggagact cctgtctgag gagggaggat gccctgtctg gtggggtgg  ggctggagga 13680
ggccgctgtc tgaggggga  ggaggcccct gtctgagggg gcaggaggtc cctgtctcag 13740
ggggaggag  gcccctgtct gaggaggag  gaaacctccg tctgaggagg gaggaggtcc 13800
ctgtctgagg agggaggagg ccttgagggg ggaggaggtc cccgtctgag gagggaggag 13860
gcctctgtct gaggagagag gaggtacctg tctgagggg  gaggaggcct ctgtctgagg 13920
ggggaggatg cccctgtctg aggggtagg  aggaggcctc tgtctcgggg ggaggagtcc 13980
cctgtctgag gagggaggag gcctctgtct gagggggag  gatgccgctg tctgagaggg 14040
taggaggagg cctctgtctg ttgggagagg aggccctgt  ctgagggtga tgccgatgag 14100
gtgatgccct gccagcgtga ggtagagaag acccaggtct gaagagggga ggatcaagtc 14160
agagaagcgt agatgcccat ctgagatgga ggaggctccc gtccgagggg aggggacact 14220
cctgtctgga agggacagag gccttcagat gaggagccag gaggcccagg cctgagggag 14280
gagaagggcc tagtctgatg gggagaaggg cccttgcctg aaggcagagc agtttcctgc 14340
ctgggaaggt catcccagcc ccacccatca gtctgaattg gacatcacca gtgcccagga 14400
cattggaggt ctgagggaaa agtctagaaa gatgatgggg ctggtcacac actaattacc 14460
aatgggaaag ctaaggtgag ttccaagttt ggcttcacca gagaaaacta atttgtgtgg 14520
cattccagaa agacctgcca aactcgatga gtgaacaggc agcccttctt cattcatgca 14580
tgcattcagt ttttgaatca ggtgagactt tagatctcac gtgaaataag tcttaagtga 14640
aacaaagaga aatttatctt ataataagag aaaattggcc gggcatggtg gctcacaccg 14700
gcaatcgcag cactttggga ggccgaggtg gatggatcac ttgaggtcag gagttcaaga 14760
ctagtctggc caacatggtg aaaccccgtc tctactaaaa atgcaaaaat agcctggcga 14820
gctggcaggc gcctgtaatc ccagctactc aggaggctga ggtgggagaa tcgcttgaac 14880
ctggtaggtt taggttgcag tgagctgaga ttgtgccact gcactccagc ctgggcaaca 14940
gagcaagact ccgtctcaaa aacaaaacaa aacaaaacaa aaaagaaag  gaaaagaaa  15000
attggccggg cacggtggct cacacctgta atgcccacac tttgcgaggc cgagaagggt 15060
ggattgcttg agtccagaaa tttgagacca gcctgggcaa catggcagaa ccccatatct 15120
acaaaaataa aataaaataa ttagccgggt gtggggtgc  acacctgtag tcccagctac 15180
tcaggaggct gaggtgggag gatcgtttga acccaggaga tggaggcgtc aatgagccaa 15240
aatcacacca ccgcactcca gcctgggcaa cagagcaaga ccctgtctca aaaaagaaaa 15300
aaaaaaaag  agagagaaaa gaaaagaaaa tgaaagaaaa aaattcaagc aaatttagaa 15360
tgatctcctt cacaaagagg cgatagtgtg agggtcactg ggaaaattag acaaaaagtc 15420
tggtctactg aaatatggtt tacatccaca tggatggtgg gctgtacttt tctccagaat 15480
tgtgtaattc ctttggccca ttgggggtca gaaaagaat  ggctaaatgt tactatccca 15540
agacacttgg attgattatt ccagagtgtg agtaaattca ggtatctctt ttaggaattc 15600
```

```
catctacttt gggctgggct tagtggctca cacctgtgat cccagcactt tgggaggctg    15660
aggcagcggg atcgcttgag ctctggagtt tgagagcagt ctgggcagcg tagtgagact    15720
ttgtacggac gaaaactttt ttttttttt ttgagatgga atcttgctct gtcacccagg     15780
ctgaagtaca gtggcacaac ctcggctcac cgcaacctcc acctcatggg ttcaagcgat    15840
tctcctgcct cagcctcctg agtagctgag attattatta tttgtttttt tgagatggag    15900
tctcgctctg tcacacaggc tgcagtacag tggtgcaatc ttggctcact acaacctccg    15960
cctcccgtgt tcaagtgatt ctcctgcctc agcctcccaa gtagctggga ttacaggcac    16020
ctgccaccac acccagctaa tttttgtatt tttagtagaa aagaggtttc accgtgttgg    16080
ccaggctggt gtcgaactcc caaccttcgg gatctgccc gcctccgcct cccaaagtat      16140
tgggattaca ggcatgagcc actgtgcctg gctgaaaaat attaaaatat atatattttt    16200
taagggattc cagctacttt gttgttatgg agatccagaa cccaattaaa gcctgtctat    16260
catgtttgag gaaagtgcag tttgagtcaa agccagtcc agtccaattt catttacttg      16320
ctggtagtgt caagctgttt ttgtttattt atatatttat ttagaggcag gatcttgctc    16380
tttcgcccag gctggagtgc agtggtgcga tcacagctca ctgcagcgtc aacctcttgg    16440
gctcaaggag tccttctgtc tcatcctcag ccttctgagt agctaggact acaggtgcat    16500
gccagcatgc ccagctaatt tttaaattat tatttgtaga gagagggtct cagtgtgttg    16560
cccaggctgg tctcaaactc ctgggctcaa gccatcctcc accttggcc tctcagagcg      16620 ctgggatgat agcaccacat ccagcctatc gagatttttt ttgtgttttt ttctttgttt    16680 tttgttttgtt tgtttgtttg tttgagaggg agtctcgctc tgtcgccagg ctggagtgca    16740
gttgcgcagt ctcggctcac tgtaacctcc gcctcctgga ttcaagagat tctcatccct    16800
cagcctcccg agtagctggg attacaggcg catgccatca cccagccta  ttttgtat      16860 taggtggttt ttaaaggcca ccgcttcttc agtgttctgc accaggtctg ggaatgttct    16920
cagctcacct agtcatgttc agaatggaca aatccctcag aggaagcaga cacggtttct    16980
cgggacggtg atcctttaga gccacatgca catgcttgct ttcttttatt attatctttt    17040
tttgagatgg agtctcactc cgtcaccgag gctggagtgc agtggcataa tcttggctca    17100
ctacaacctc tgcctcccgg gttcaagcga ttctcctgcc tcagcctccc gagtatctgg    17160
gactacaggt gcccgctgcc aagcctggct aattttcata tttttagtag aggcgcggtt    17220
ttgccacatt ggccaggctg tctcgaactc ctgacctcaa gtgatccacc cgcctcggcc    17280
tcccaaagtg ctggaattac agatgtgagc cactgtgcct ggccaaatgc tttcgtttct    17340
ttaaaaatca aagggaaagg aatgactata atccagtctg cattgtatat gtccttatac    17400
cagtacattt gtgggatata attttagtt cttttatgg agaagaagtt cccaaggcag       17460
atgtgtctgg ggctcgtgaa aattcatcct gaagtcctcc atgtccggga tgtatttcac    17520
tgctaggaat ccctcctggg cagaggtagg atctaaaggt gtgaccgctg aggaagtagg    17580
tcggctctct ttttgtttgt ttttgtttt tgttttcaga tggagtctgt ctctgtcgcc      17640
tgggctggag tgtagtcgtg tgatctcagc tcactgcaac ctccacctcc tgggttcaag    17700
tgattctgct gcctcagcct ccacagtagc tgggatcaca ggcacgcgcc accacaccca    17760
gctaattttt gtgtttttag tagagatggg gtttcaccat gttgtccagg ctggtctcaa    17820
agtcctgacc tcaagcgatc cacccacctc agcctcccaa agtgctggga ttacaggggt    17880
gagccaccgt gcccagcctt aattttgta ttttagtag agatgggttt caccatgtta       17940
gctaggctgg tctccaactc ctggcctcaa gtgatccacc tgccttggcc tccctaagtg    18000
```

```
ctgggatttc aggcatgagc catggcaact ggcctgctct gttctaaatg cagatctaaa    18060 cccctgcag gtaacctgga tgaggacatc attgcagaag agaacatcgt ttcccgaagt    18120
gagttcccag agagctggct gtggaacgtt gaggacttga agagccacc gaaaaatggg    18180 taaggccggg gtaccccgg tacaacccac cccagagtca gaccgtttaa tttgcatgca    18240
cctgctatct ctggtcttct ctggaatcac agtgcaaccc cacagcccaa cctagaaaaa    18300
tcaggaattg ggtgacctac atggaggcac cccagaccc ttccagcctg tcccttgggg    18360
tccctctgca ccagttcttc ccctctacca ccctgctaga tgacatctcc taataccccca    18420 acctcttctc catccagaat ctctacgaag ctcatgaata tatttttgaa agactccatc    18480
accacgtggg agattctggc tgtgagcatg tcggacaaga aggtgagag aggatgctgg    18540 ctggtccccg ggaggcaggg accccagggt gtctgagtgt catctcattt tatccaaact    18600
caatcaaccc tatgtttctt ggcactttat tctctgccct ggttaccaca gaggtgttgt    18660
taccaggaac tgtgggaatc cttagttcct gtctaacttg gaagaaagaa ttcagccaag    18720
agtcacatag caagggttaa gtagcagagt ttattgaagg aagaaacagc tctgggctgg    18780 tcccctgga aaatagtag tagcaatgct tatttaaaga gacagggcca gcctcgatgg    18840
ctcacaccta aatcccagc actttgggag gctgaggcag gggaatcact tcaggtcagg    18900
agttcaagac cagcctggtc aacgtggtga accccgtct ctactgaaag tacaaaacaa    18960
ttagccaggc aggggtggc gggcgcctat aatcccagct actcgggagg ctgaggcagg    19020
agatttggtt gaacccggga ggtggaggtt gcggtgagct gagattgtgc cactgcactc    19080
cagcctgggc aacaagagca aaactccttc tctaaataaa taaaaagtga ccgtatgctc    19140
tgaaagacga cacagacatg gctgctcaac agaacgagcc agcagcagat actgctggta    19200
gactcttttt atgagactct tacatgattt ttcgtgaagg ggcgtgagtg ggtgtcactt    19260
gtaagcatgt tttgggaggt ctctttgggc gagcaggctc tgtggctgta ggtactagca    19320
tgcacgtggc atgtctcatt agcatcgaaa atctccaccc agaggtgtgt tttttactat    19380
gataatgagc aaaacacaac tctagggtgt tttcggagca gtgcacatgc tcatcatcgg    19440
ggaaaatccc tagcaaagtt atttccagct aggacctgat aagtccccctt cagggccaga    19500 ggaccccaac cacaaggcca tgtgtagcta aagtagccat cgtcctttc gctgactgcc    19560 agtgagcagc gctgtcagta ggcagcctgt ctggacttc ttttcccaga aagctcccct    19620
gcctgctcat ttccgcctat ctgcctactc taacagtgtc aaaagctaga cagggtgggg    19680
gtacagtctc taaaattgat gcttttcttt ctttcttttg tttttgagaa ggagtctcac    19740
tcggtcatcc agccataatt tatatggttt attataattt ataataaatt taattataat    19800
atttatttat atatttatta attgtaatgt ttataattat aatatataat tatatattac    19860
ataatatatt tcatatctac atatcacata ttacatatgc aatatattat ataccacata    19920
ttacatatat aacataccac atattacata tataatatat catatattat atattacata    19980
tataatatat catatattat atattacata tataatatat catatattat atattacata    20040
tataatatat catatattat atattacata tataatatat catatattac atatattata    20100
tattacatat ataatatatc atattacata tattatatat tacatatata atatatcata    20160
ttacatatat tatatattac atatataaca tatatattac atatatcata ttacatatat    20220
catatattac atatataata tatcatatta catatatatc atatattaca tatataatat    20280 atcatatta atatatatca tatattacat tacatgtta atatgttata ttacatataa    20340
tatatattgc atatcacata tataatatgt tatatgttgc atattacata tataatatat    20400
```

```
tatatattgt atattacata tataatatat atgtaatata tacatattac acatgtaata   20460
tattatgtaa acatataata tgtattataa tttataagaa atttaattat aatataattt   20520
aatgaattat aataaaccat aattcattat aatttaatac attataataa accataattt   20580
attataattt aattttgttg taatgtataa ttataatttta ctactaatat gtcatttgtt   20640
attgttgaca tgttaacata tataatgtat attttattag atatataata taatgatgt    20700 atcatttatt attgattaca tatctataat tataccatat cataacttat tacaaaacat   20760
tctatttaat ttaaatatac ccaaaatagt atcatttcaa cattttgtaa aaagttgcaa   20820
aaccacaacc cactaataat gtgactataa ccttttaata tttgataata atctactagt   20880
atatcaaaat tactgatgat atattttact tctgtttgca ctaagtcttc aaaatccagc   20940
atgtgtttta caattcagtg catctcattt aggatactag attttctttc ttttttttt    21000 ttgatacagg agcttgctct gtcacctagg atggagtgca gtggtgtaaa caggatgcta   21060
agttttcttt ttttagtaga gacagggtgt caccatgttg gccaggctgg tctcaaactc   21120
ctggcctcaa gcaatctgcc ttcctcagcc tcccagagtg ctggaattac aggcgtgagc   21180
caccgcgccc agcgcaggat gctaggtttt cactggaaat actttgatct gtattttagg   21240
tttcataaaa tttacagttg aaaaggtaga ttctcaggcc gggtgcaaag gctcaagcct   21300
gtaatcccat tactttcaga ggctgaggcc ggcaaatcat tgaggtcgg agtttgagac    21360 cagcctgggc aacatggcaa agcccgtct ctacaaaaaa aaaaagaaa agaaaagaaa     21420 agagaaagaa aaggtagatc ctcatactca agtagttgca aaaatactta aacgttttcc   21480
actcaatcat catttttaaa aaattaagat ttaattcact tactatatgt caccctttta   21540
aaatgtacaa ctcaggtcgg gcacggtggc tcacacctgt aatcccagca ctttgggagg   21600
cccaggcagg cagatcacct gaggtcagga ggtggagaac agcctggcca acatggtgaa   21660
accctgtctc tactaaaaat acaaaaaatt agcaggacat gcgggtgggt gcctgtaatc   21720
ccagctactc aggaggctga ggcaggagaa ttgcttgaac ccaggatata gaggttgtag   21780
tgagccaaga tcacgccact gcactccagc ctgggtgaca gagcgagacc ccatctcaaa   21840
aaataaataa ataaaaaata ataaaatata taattcagtg gtgtttcata tatttaaaat   21900
gagcatcagt tgttgttttt gtttcattgg gtttggtttt acagacagga tctcactctg   21960
ttgcccaggc tggagcacag tggtgcgatc atagctcact gcagccttga actcctgggc   22020
tcaagcaatc ctcctgcctc agcctcccaa agtgctgtga ttacaggcat gagccaccgc   22080
acctagctag atcatcaggt ttaaagttta agtctgaatt aaattaaata catttaaata   22140
caagtacatc aaataaaagt acaaatccag tttctcactc aggcaaaccc catttcaagt   22200
gctcagcgct cccccacagc ttggggctac catatcagac aagcagatat attttggaga   22260
tttctcttcc tccctacacg tagatctctg agtcaaacta caaacagaat gtaaatcatt   22320
aaatagtggt aactccggcc aggcgcagtg gctcacgcct gtaatctcag cacttgggag   22380
gctgaggcgg gtggatcgtg aggtcaagag atcgagacca tcctggccaa catggtgaaa   22440
ccccatctct actaaatata caaaaattag ctggacatgg tggtgcgtgc ctgcagtccc   22500
agctactcga gaggctgagg caggagaatt gcttgaaccc aggaggcgga ggttgcgttg   22560
agccgagatg gcgccactgc actccagcct ggcgacagag tcttgctctg tctcaaataa   22620
ttaataataa taataataat aataataata ataatggtaa ctcccagcca   22680
ccaccatcat catctgtcat ttgtcgccat tgacagcgtt tagttcacag gcttcagcaa   22740
agacaggctg agttagggag agctcctgcg gagtggacta agagctgaga cccaggagcc   22800
```

```
tggccttgtc cactccccga ccttgacact ccgtgttctg tctctgcccg agcagggatc    22860
tgtgtggcag acccccttcga ggtcacagta atgcaggact tcttcatcga cctgcggcta   22920
ccctactctg ttgttcgaaa cgagcaggtg gaaatccgag ccgttctcta caattaccgg    22980
cagaaccaag agctcaaggt gggtcccggg gtggcagagg cttcttggag gctgccaggg    23040
ggtaggtagc ctgttgcaca cacacttgcc cggatccttt ctctccctgg caggtgaggg    23100
tggaactact ccacaatcca gccttctgca gcctggccac caccaagagg cgtcaccagc    23160
agaccgtaac catccccccc aagtcctcgt tgtccgttcc atatgtcatc gtgccgctaa    23220
agaccggcct gcaggaagtg gaagtcaagg ctgctgtcta ccatcatttc atcagtgacg    23280
gtgtcaggaa gtccctgaag gtcgtggtga gtgcttgggg cacccacaaa cccttgtcct    23340
tcagagaggg ctcctggtct tcgtactatt gactcaggtt ggagatccag gctctgagac    23400
actaagaatc atagtgtcca gcttaggaaa tttggaagtc ccagaatttc agaagcagag    23460
ccaggattgg ggtaaagtga gtgagatgac cccaggctta gaattttagg tggtgccaaa    23520
aacctcgtcg accatcacca atcaataatt ttttatact cgatttgaaa ttttttattt     23580
atttatttat ttgtttgttt atttttttga gacagagtct cactctgttc cccaggctgg    23640
agtgcagtgg cgcgatctca gctcactgca atatccgcct cccgggttca cgccatcctc    23700
ctgcctcagc ctcccgagta gctgggacta caggcgccag ccaccacgcc cggctaattt    23760
ttttgtattt ttagtagaga cagggtttca ctgtgttagc caggatggtc tcgatcttct    23820
gacctcgtga tccacccacc tcggcctccc aaagtgctag gatcacaggc acgagccacc    23880
gcgcccggca atgctagggt gatcctaagg acagtgccct gctgaccatc tgtgtgtctg    23940
tctgttcttt tattcatcca acgactcccc ccacctctaa cactgcgtag ccggaaggaa    24000
tcagaatgaa caaaactgtg gctgttcgca ccctggatcc agaacgcctg ggccgtggtg    24060
agtcggctgc aggggagggg gctgagggc tggcagggta aggggggtaa atgacctggg     24120
tttagtgagg taggatagggg cgggagggag ctagagccat cggtatctct cactcaccct   24180
gcagaaggag tgcagaaaga ggacatccca cctgcagacc tcagtgacca agtcccggac    24240
accgagtctg agaccagaat tctcctgcaa ggtgagacac ccttgacccc gaccccatgg    24300
gtcccaggag ggcatggatg gagccaaatt ccatctcatt ctggaggtgt ttaacccgca    24360
cctttctctt ccccttcagc tagaacagcc catctgtgat ctgttttccc tcttttacat    24420
tttttttttt tttttttttt gagacagagt ctggctctgt cacccaggct ggagtgcagt    24480
ggcgcgacct cagctcgctg caagctccgc ctcccgggtt cacgccattc tcctgcctca    24540
gcctcccgag tagctgggac tacagccacc cgccaccacg cccggctaat ttttttgtat    24600
ttttagtaga cagggtttt caccgtgtta gccaggatgg tctcgatctc ctgacctcgt     24660
gatccacccg cctcagcctc ccaaagtgct gggattacag gcatgagcca ttatgcccgg    24720
cctaaaaatt tttttaacca tacagatatt atttgctatg atcggtttta tagaagcctc    24780
cagatagcat ttagttcagc aaagagcttt cgctgataca tcagtttatt ttaattttc     24840 tagaccttct gtgcttctta gatgggaaac cagcttaaat gagactcaat agcctgtaat    24900
cccagcactt tgggaggccg aggcaggcag accacctgag gtaggagttt gagaccagcc    24960
tggccaacat ggtgaaaccc tgtctctact aaaaatacaa aagttagctg ggcgtggtgg    25020
cacatgcctg taatcccagc cactcgggag gctgaagcag gataatcgat tgaacgtggg    25080
aggcgtaggt tgcagtaagc cgagatcagg ccactgcact ccagcctggg cggcagagca    25140
agactttgtc tcaaacaaaa acaaacaaac aaacaaacaa aagacaagc aacatagtac     25200
```

```
aagagcagaa attctggagg tcatttcttg ccccaggagg gaagactgga gaaagaaagg   25260
gacttgcaac ctgtaagcta taaggctttg gggcaagagc cttggttttt tcacctttgg   25320 tagggtaga ataatagtat ctacctccaa gggttggtgt gatgatttt ttttttttt      25380 tgaggcggag tctcactctg tcgccaggct agagtgcagt ggcgtgatct cggctcactg   25440 caacccagc ctcccgggtt caagtgattc ttgtgcctca gcctcccaag tagctggac    25500 tacaggcgcc cgccaccatg cccactaatt tttgtatttt tagtagagac ggtgtttcac   25560
catattggtc aggctggtct tgaactcctg acctcaggtg atccaccac cccagcctcc    25620 caaagtgctg agattacagg cttcagccac ggcgcccagc ctcgttgact attaagtgag   25680
acactctatg gtattctctt agaacagtct ggaaagtaac attaagcgtg atataagtat   25740
tcctgaatat tgttactgga attattttac tgctggtgaa atgagaccca aggaccaggg   25800 tgccctgtg aagcacctcc cactcctaac agtgcagacc cccgaacagc cactcagcca    25860
tgcagcctcc cctccccgca gtcacatcct ccccagtcct cgcctgtccc taaccccttg   25920
gccctggctg gttgggaggc tggaacccctt ttcacgccac ccaaggtgg gtcacccacc   25980 tggcttgagc aacgtcctct tcccacctgc tgcagggacc ccagtgggcc agatgacaga   26040
ggatgccgtc gacgcggaac ggctgaagca cctcattgtg acccctcgg gctgcgggga   26100 acagaacatg atcggcatga cgcccacggt catcgctgtg cattacctgg atgaaacgga   26160
gcagtgggag aagttcggcc tagagaagcg gcaggggggcc ttggagctca tcaagaaggg   26220
tgggctccct gccctcttg gagacccag ggaccccttt ccgagcgcat ccctccccta    26280
agatcccacc tcatctcaag accacgccct ccctgaggc tccaccttct ctcctagcca    26340 ctccctcat ttgaggcccc acctcttctc aaggctacgc cctctgaggc cctgactcct    26400
cccaggccag gcttttcatg agaccccgcc tctcctcaag gccatgccca tcccctgagg   26460 gcccccacc tcttctcaag gccacgccct ctgaggccct gactcctccc aggccaggct   26520
cttcatgaga ccccgcctct cctcaaggcc atgcccatcc cctgagggcc cccacctct    26580 tctcaaggcc acgccctctg aggccctgac tcctcccagg ccaggctctt catgagaccc   26640
cgcctctcct caaggccatg cccatcccct gagggcctcc cacctcttct caaggccacg   26700
ccctctgagg ccctgactcc tcccaggcca gaatctcgag accctgcctc ttttcaaggc   26760
cacgcccatc cctgggtcc ccacatcttc tcaaggccac accttctgt gaggcgccac    26820 ctcctgtccc agccactctc atctgaggcc ccacgtcctc tccaggccat gcctcttccc   26880
tgagactcca cccctctct gagagccctc cctcccctga aagcccccca ccctcaatat   26940
ccttctcctc tctgaatccc ttgtcctctt gagaactttt ccactcctc gttctgatcc    27000 cccaccctct ttgagtcctt ccctttttaa ggtcccctcc tcccagaacc cctccgccac   27060
cctgagcccc tgtcccctct ctgcaccccg ccctgccct ttctggcgtg cccctctgc    27120 tcagcccgg ctcttttggg ggttcctctc tcttctctgc agggtacacc cagcagctgg   27180
ccttcagaca acccagctct gcctttgcgg ccttcgtgaa acgggcaccc agcacctggt   27240
gagtcccaac agccagctca ggccatgcat actccccacc ctcaaccccc agcagggccc   27300
ggaccctggc caggggtggt cccttaggcc agccttgccc aaacagccct ggacctgcag   27360
agtccaggca agcgctggct gagtggccgg cggtcattaa gcatccttaa gcacggaccg   27420
catacaacag ctgggtcctg gggcctggga aggcaaacca ggcaaactgg gccaggccct   27480
ggtccctccc ccacgctcat tggctggttg acatggcagt ctctggatct cagagccgat   27540
tggctcatgc tctgtgccca ctccaggctg accgcctacg tggtcaaggt cttctctctg   27600
```

```
gctgtcaacc tcatcgccat cgactcccaa gtcctctgcg ggctgttaa atggctgatc   27660 ctggagaagc agaagcccga cggggtcttc caggaggatg cgcccgtgat acaccaagaa   27720
atgattgtaa gaggctggga tttagggcaa aatggaagag aggggctcct gagtctcgca   27780
ggatgaacac gagagagagc cccacctcca tgtgcccact gcccaattcc ctttgcaaag   27840
attgggctgg gggtggggg caggcagata tatgagccag aggcgtcact ccagcattgc    27900
aaaaaccaga gacctgcgaa gcccagcgca aaatgaagag acacggcccc tcgctcagaa   27960
attattaaga atttcattaa accaagtgca ggggtcctgc ctgggaatcc ctttctcaca   28020
ttcaatccat caacacctgc attctcccat gatgttataa gaatcacctc cttctctcca   28080
tccttatggc cagcccctgg tccaagcaac actctcccg cccctcctta tttggagacc    28140
ttgtagaaac cacctcctgg tcatcatcct ggtggcctcc cacttttgtt ggctctcaga   28200
cactcaccac atagcagttg gggtgatttt ttcaaatcca gctggatcag ttcttagaaa   28260
gtcccgtggc tcccctgtg gcacttaaac acaaaactcc ttcgagcact ggttctcgaa    28320
gtgtgatcct cagaccagcg gcagcaacag cacccatgac ttactaaaaa tgtgcattct   28380
gtggctgggc tcgacggccc atgcctgtaa tcccagcgct tgggaggcc gaggcaggag    28440 gatggcttga gcccaggagg tcgaggctgc agtgagccat gatcatgaca ctgcactcca   28500
ggctgataac agagtgagac cctgtctcaa aaacaaaaca tattctgaga ccggacccca   28560
gactcactga atcagaaatt ctaggggcag gacccaggaa tctgaggggt gtgagtgtgt   28620
gtgtgtgtgt gtgtgtgtgt gtgtgtgtgt gtgtgtgtgt ttgagatgga gttttgctct   28680
tgtcacccag gctggagtgc aatggcccga tcttggctca ctgcaacctc cacctcccag   28740
gttcaagcaa ttctcctacc tcaacctcct cagtagctgg gattacaggt gcccgctcca   28800
ccatgcccag ctgattttg tatttttagt agagacgggg tttcaccatg ttggccaggc    28860
tggtcttgaa ctcctgacct caggtgatcc gcccaccttg gcctcccaaa gtgctggat   28920 tacaggcatg agccaccgcg cccggcctag gaatctgagt ttttaaaagt gcccgcattc   28980
ctccaggtga tgctaatgtg tgcttgagat ggagaatcac tgcctcagtc tcacctttca   29040
ggcttccaga cttccagcct ttcttttctt tccaggctcc atccattgat aggagccttg   29100
ctctattgtt ctacagggcc tttgcacatg ctgtttctgc cacctagtat gctaatccct   29160
gccgtctgtg agagttgact ccctcaggga cactttttct gacctcccca actgggtcac   29220
actcccacag ttcattatcg ctgcgatgtc ctctttccct tgcacagaac tcatccactt   29280
ataagtatat atctcttggc tgggcgcagt ggctcatgcc tgtaatccca gcactgtggg   29340
aggccgaggc aggtggatca cctgaggtca ggagttcggg accagcctga ccaacggggg   29400
aaaccccatc tctactaaat acaaaaaaat tagcttggtg tggtggtgca tgcttgtaat   29460
cccagctact tcggaggctg aggcaggaga attgcttgaa tccaggaggc ggaggttgca   29520
gggagtcgag attgcgccat tgcactccag cctgggcaac aagagcaaaa ctgtcccaaa   29580
aaaaaaaaaa aaagtgtat atctcttgag gagctggatg gaccatgtcc atcttcccta   29640
ctagacaaaa gctctgtgag ggctagagcc tgtgtctggt tttacaatgg atcagaccgt   29700
tgtacccatt gtacattgca cattgtacat tgacatttgc agaaggaaca aattgttgca   29760
tgaattaata ctaagaagtt tgaccttcct agggtagcgg ggtaacacct agaagagact   29820
cagccctgcc cagacccct gattctgaat ctgcaagggg ggatgactgc catgtgtgga    29880
cacaccggtg accccatcct tgctttctgc tctctatctc agggtggatt acggaacaac   29940
aacgagaaag acatggccct cacggccttt gttctcatct cgctgcagga ggctaaagat   30000
```

```
atttgcgagg agcaggtcaa cgtaagtgcc ctccatcttc ccaccctacc ctaccttacc   30060
cgatgcagag cacagccacc ttggagagtg agaggttgcc ttcagggaat ttgcagctct   30120
cccagtgcaa taacagacat cactgcagtc atgttaatag ctaacatctt ttgagcactt   30180
aactcatcta atacagaccc gccctctaat agtttcacat gttaagtctc ataatccttt   30240
tagcagcctg aaaggtaagt cactcttatt atccccagtt tgcagatgag aaaactgagg   30300
cacaaagaga tcaaaggtgg ggattctttc tgtctgcctt acaattttca gagggttttc   30360
agcccatttc caaaagtgct ttctacatca gtgctcatg atcagtacag ttgcgtactt   30420
gctacttcct taaagaaaac ttgggataca gagctaagac tatttcctta gtccagagga   30480
tctttcaggt gattttcaaa gggatccgtg actccaaaca ggaaacggtg aacactgttg   30540
gctcatcact gtctcttttt cctctggttt tgattctgaa gcaggaagc ttggaaagat   30600 gggccgctga gagtctggaa tgcctttgtc tgctttattg tggttgtttg tttgtttgtt   30660
tattttttgt gatggagtct cactctgtcg cccaggctgc aatgcagtgg catgatctca   30720
gctcactgca cccttgcct ccaggttca agggacttta ctgtttcagc ctccagagca   30780
tctgggatta caggcacccg ccaccatacc cggctaattt ttgtcttttt agtagacatg   30840
aggtttcacc atattggcca ggctggtctc gaactcctga cctcaggtga tctgcctggc   30900
gtggcctccc aaagtgctgg gattacaggc atgagccact gcacccagcc taattgttgt   30960 attttagta gagatggggt ttcaccatgt tggccaggct ggtttcgaac tcctgacctc   31020
aagtgatcca cccaccttag cctcccaaag tgctcggatt acaggcgtga gtcactgcac   31080
ctagctgatc gtggggtttt gagtgggttg tttaacgttt agctttccaa gtgggaagcc   31140
caggattcca ccctcagcta gtggcttctc ccccttagg aaaagagatg gaggggaggg   31200
gccagtgaag agaaaaacaa acacagggct gttgcctcta cacccaaga gggaccaagg   31260 cagagagaga gagagagaga gagagagagg gagggaggga gggagggagg gagggaggga   31320
ggtaggtaga gagagagaga gagagagaga ggagaggtgg ggtcagacaa atctgacttc   31380
aaatcctgac tcatgggcac ttccaccctt gagcctcact caggatgtgc atctgtaaat   31440
tggggataat aaataacgat ctctgtattt ttaggcctct gagttgtccc agatataaca   31500
cacatgtgac ccagattata caaaaattga tgggggaattt atgtgcaggc accaaggcat   31560
caaatagaga tgaaggtggc ctcagggact ctgccaggat gctttgctcc tctctcccgt   31620
gatcttcatt ccgttcttgg ccaataattc agttcaggca gaatatggct gccttcctta   31680
gagaaaatat cagatcaagg ttagggccgc catattccca ggaaaggact ctgattggct   31740
cagcctgggt cagatgacta tatctggacc aatcagctaa ggacaggaag taggtctcag   31800
ggggcagaca tggctgtttc cactgtggcc acgtgaatgg aagggagaag aagttcttac   31860
aaaaggagtg gatgtcagag aggcaaatgg gcaggaataa aagagatttg tttctgctac   31920
aacatagcaa cattgtagca gagtatagca caggctgtga aaccagactc ctggggtcaa   31980
gagtgtgctg taatcccaac tactcaagat gctgaggcag gagaatcact tgaaccaggg   32040
aggtggaggt tgcagtgagc cgagattgcg ccactgcact ccagcctggg caacacagca   32100
agactccttt tcaaaaaaaa aaaagtgtg ctataactag cttgctggag cccagtgtta   32160
aatttccagg aattttttcaa gctggtcatt aaatacaatt attattaaaa actaaatatt   32220
aggccaggca cagtgagcct gtaatcccgg cactttggga agccaaggcc ggcagatcac   32280
ctgaggtcag gagttcaaaa ccaccctggc caacatggca aaaccccgtc tctactaaaa   32340
atacaaaaat tagccgggca tggtggaggg gggcgcctgt aatcccagct acgcaggagg   32400
```

```
ctaaggcaca agaatcgctt gaacccggga ggcggaggtt gcagtgagcc gagattgcgc   32460
catgcactcc agcctgggcc agagcgagac tccgtctcaa aaaaaaggcc aggcgcggtg   32520
gctcacgcct gtaatcccag cactttggga ggccgaggtg ggcggatcac gaggtcagga   32580
gatcgagacc acggtgaaac cccgtctcta ctaaaaatac aaaaaattag ccgggcgcgg   32640
tggcggacgc ctgtagtccc agctactggg aaggctgagg caggagaatc acttgaaccc   32700
gagaggcgga gcttgcagtg agccgagatc gcgccactgc actccagcgt gggcgacaga   32760
gcaagactcc gtctcaaaaa aaaaaaaaag caacaacaaa aaacccaacc aaccaaccaa   32820
acaaacaaag ttataaaagt tacagttaaa taaattatat taaacacaaa ggttagaaac   32880
actcaaactc atcgcttcct aaacgcctta ctcccataat ctatactctt ggggttactt   32940
atgtctgttg gatctgtata gtgaaaatac tatataatac tgtggtactg caaagctctt   33000
cccaactcta cattcaacga caccatattg gtaggttgaa atcagtgatg gaagtattta   33060
catcatggaa atgagaaaac agtacaaatc atgtcttccc ccatcccccag aaggctgtgt   33120 ttggatccta actctgccac ttatttccta ggtggtcttt gcaaaattac tgcatctctc   33180
agggctcagt atgctcatca ggttttatga gattaaatgt gtgggtatct gaatgacaca   33240
aagtaagtgt gagctatgat gatgaagaag ataaagatga tgatgacgat gatgatgatg   33300 actgatgag gtgttcacag tggtatactg aatctggcgc atactagttt atgagtaaca   33360
atttggagaa tgtctcccca ggactttgtt cagtgatgtc gcattgacac cgtgaaattg   33420
gcccctggtg ggagtattta caccacagaa attgtaaatc attataaacc aaggatccct   33480
caaccctccc actggagagc tggctgttaa acttttacca gcacaccacg gggtacgtgg   33540
atttctccag atacataata gatatgcagc aacaaggcag ctcatggtgg ctaaaatatc   33600
tgggaaattc tcaaaaatgg acaaatctaa dacaggtgtg tcccaaggac agaaatccct   33660
gatgctcagg aagtgctgct cgaatgatcc ttactaacgt gacagcaatg cccacatgac   33720
cggagaatct gatcctcttt ctcatagagc ctgccaggca gcatcactaa agcaggagac   33780
ttccttgaag ccaactacat gaacctacag agatcctaca ctgtggccat tgctggctat   33840
gctctggccc agatgggcag gctgaagggg cctcttctta acaaatttct gaccacagcc   33900
aaaggtgagg gttggcctgg aggggtgaag ggagatgcat ggctgaagtt cagggcggga   33960
gatactgagc tgggatgcat ggcttttagc tgagctggga cagatgaccc taagccaagc   34020
tgagatggat agtcctaagg tatcaagctg ggatgcataa ccctgagctg agctgggatg   34080
cacggctcta agttttcgca ggtcctcatt gtaaaccaca cgagaaagtt tgttgcgtca   34140
tttattcaac aaatgcgtat taagcattca tttcaaaggg agaagtgaga gttgatgaaa   34200
caagagaggt aaggcaggag ccaagtaatt gagagcctcg aatgtcagcc aggacaccca   34260
aacaccagga agtctagcat gcatctcttt ctgagctttc tctgagccat ccccaggctg   34320
gacagagcag tgagcactgg ggatggggta tcttctttgc agataagaac cgctgggagg   34380
accctggtaa gcagctctac aacgtggagg ccacatccta tgccctcttg gccctactgc   34440
agctaaaaga ctttgacttt gtgcctcccg tcgtgcgttg gctcaatgaa cagagatact   34500
acggtggtgg ctatgctctc acccaggcaa gtgggcccac agcccctagg cacatgcatc   34560
cctgtctcct gcggcttccc actggcctcc tagagaagac actgaggccc agcgaggcag   34620
ttcttcattc ccacgagcca gtgtgattgc agtggagttg agaatcagtt tttattactt   34680
gcaaacccat ctataggttc tagaatacaa tctgggtact ccaagctgtg tgttgagcct   34740
tcttcttgcc ccaggtgtct agatcatgtt ctcagggccc aggttcaggt ctaagcctct   34800
```

```
ctctccacct ggtgggctct agaccaggtt cccagttcta tctcacaatc ttaccctgtc   34860
ttgctggtgg gttctagacc atgttcccag ttctaccagg ctcccaatgt cacattgcct   34920
cactggcggg ctctatagta tgttcccagt taccctgggg cattacgcaa accctcttct   34980
aggccatggt ttcagtaact tcaggcttca gcaacttcag gctccagttg gcctcctttc   35040
tttctggtgg tctgtcactc acgttctcag tgttacagtg tcactcttgg gttgtagatt   35100
atatgctcag tatcctctgg ctacggtttc attctgttct tcatgagtgg gttctagaca   35160
tattctcagt gtctccaagc cctggtctaa gactctctcc tcttgatggg tctagactgc   35220
atcctcaggg tcgctagaca ttcagtctta catttggact ttctgatgga ttctagacat   35280
gttctcagca tctccaagtc ctggtgtaag tttctgtctc tcggagagtt ctgaacatgt   35340
cctcagagtc cagtgacctc cagttatcac ccctgcactc tctagtaggt tctaggccac   35400
attttgatgt cccagctctg atttgaacct ctttatcccc cactggattc tagccacttt   35460
cccaggctcc cagatcacca tctttctctc ttgtgggttc taggccacct tcatggtgtt   35520
ccaagccttg gctcaatacc aaaaggacgc ccctgaccac caggaactga accttgatgt   35580
gtccctccaa ctgcccagcc gcagctccaa gatcacccac cgtatccact gggaatctgc   35640
cagcctcctg cgatcagaag aggtacagtc acccagccaa gccctcctca ctctggctgt   35700 ctcccccctac actagccagg gtttactggg aagcaagagg gagggccagg tgaccatcac   35760
aggcagcaga aggcttaatt cccaacatgc tctcttctct cttttcactc tgcagaccaa   35820
ggaaaatgag ggtttcacag tcacagctga aggaaaaggc caaggcacct tgtcggtaag   35880
gaacagaaac ccacacctgc ctggcccatg cccctctgcc ccagagggac catctcctct   35940
tgtccccagc agtcctagtc ctgtgggctg acattgtgtc tcctctccca tcttaccagg   36000
tggtgacaat gtaccatgct aaggccaaag atcaactcac ctgtaataaa ttcgacctca   36060
aggtcaccat aaaaccagca ccggaaacag gtaaaaggaa tcaaggcctt atctgtcacc   36120
ttcctcctac ccctcttcta atgtcttccc cgctcctgaa tcaacacaca ggtataccct   36180
ctcccatctt tctctcttct gtgtttctag aaaagaggcc tcaggatgcc aagaacacta   36240
tgatccttga gatctgtacc aggtaagaag ctaggtcacc ggggttcatc ttggccatcc   36300
ctctatctct agcaagaatt cttgcaaata atatccatga tattcagtac tttccaagta   36360
cactgtgtat ctgatactgt tctaagtatc caccatgagg tagacaacac agacagtcct   36420
tgctttgcat gttaatgtga gaccacagca atgaccacgt aagctgagac tgtcaaagca   36480
tcttagtaat caatggagga aagtacacaa tcattccatg acctttaaag ttttcttttt   36540
ttctttttag agagataggg tcttgctctg tcagccaggc tggagtgcag tggcacaatc   36600
atagctcact gtaacctcaa actccctggc tcaagcgatc ctcctgcctc agccactcaa   36660
gtagctggga ctacaggcgt gtgccatgac acctggctga ttttattttt ttattctttc   36720
tagaggcagg gcctcactgt gttgcccagg ctggtctcga actcctagcc ttgagcattc   36780
ctctgccttg ggctgccaaa gttttgggat cacaagcatg agccactatg cccagcctaa   36840
atgtttctat tacaacattt aaaattatca tactgccagt tataaagata cagggaaatg   36900
gccgggtgtg gcggctcgcg cctgtaatcc cagcactttg ggaggctgag gcgggcagat   36960
cacgaggtca ggagatcgag accatcctgg ctaacacggt gaaacaccgt ctctactaaa   37020
aatacaaaaa aattagccgg gcatggtggc gggtgcctgt agtcccagct acttgggagg   37080
ctgaggcaga gaatggcgt gaacccagga ggcggagctt gcagtgagct gagatcacgc   37140
cactgcactc cagcctgggc gaaagagcaa gactctgtct caaaaaaaaa aaaaaaaaa   37200
```

```
aaatagaata aaacaaaata aagatacagg gaaatgaaat tcatagtaag atgagtattt   37260
gactacaccg taatttaaaa cattagaaca ttgagatgca aggtgtattt gttgtttttt   37320
ttttcctttg tatgacactt acggagagta ctttagttca aaaaaatgct tgccttcttc   37380
tctttgtata atttacaaca tggagtaaac atcttttcta tgccttagta ccttgtcttg   37440
ctcctttcta gtttggatc agcttccaat attttatcct ttgagctttc catgacacaa    37500
aattcctcca agagttcctt taaagtgact ttgtattcta taatgtccct tcctctggga   37560
catcttcatc cttttttgtcc ccatgacctt ccttatttat gctaatacat ttgccttccc  37620
tgagttcctc tacactacct atctctcaaa tggcagcagg gtcaacatca ccatagtctg   37680
ctattctttg ataactccat ttatgctgtc tttgaagttc acttctggca ttatcacttt   37740
tcatttcttt gctgcatttt tatctttgtt ggccagttcc ctcttttcgt gatacattgt   37800
tgtaaaatct catgggagtt agccacctgg agacagggag gcaacagaac tacacacttt   37860
gctgtctgtg cataaattga agagcagaag ctcagtgacc aatcactgat ggactttgaa   37920
aggagtgaca gtaattggcc ctcaattatg atgcttatct tttatttatg tcgtgatttc   37980
tagactgaag agttagcaac aaagtttata ccatatgcaa ctactcgtga tcaatatacc   38040
aaggtactga aaaagaacca tgtcactggg ctactagtgt tatttaactg aatcatgcag   38100
agtgagggct gcctgtattc ttgccttgtt ttctagaact gaagcatgga gggtcaaata   38160
atgcatccaa tgttatttag agctggaatt tgaatccatg cagttgggtg cagagtctga   38220
gctcttaatc accttgacca ttacattacc ttgcttttta tttcctttgg ggaaatgttt   38280
cctaaaaaat gtaacgcccc tctgtgctgc tatgtgggaa tcagaagtct cagtgcctga   38340
tcagacctcc ttgtccagga acagacccctt ggggctgacc cctccttggg acccaatgcc  38400
cttcttcctg cactatccag gtaccgggga gaccaggatg ccactatgtc tatattggac   38460
atatccatga tgactggctt tgctccagac acagatgacc tgaagcaggt atgaagggct   38520
caggagctgg gataagtgga aaggagcctg ggttctggaa gaggctgcag ggagagaggg   38580
gtccaggagg gattttttcac aggctccacc tttccccagc tggccaatgg tgttgacaga   38640
tacatctcca agtatgagct ggacaaagcc ttctccgata ggaacaccct catcatctac   38700
ctggacaagg taaggctgca tcatcctccc ctgggaggct tccaggggca ccctgacctc   38760
tatctggctg gtctttctttt tcctttcagc ttttgtctct gggtcagact aaccctgggc  38820
cagaggagac agggtctgtg ctgctgagtt gtaggggaag gagcttgtaa aataagggggg 38880 tcaacccagc atcttctata aacatctcat cttctgacca tttgcctcct ccaacttgtt   38940
atcagagtct taaacaacca ttgaaaaaaa gccctttttgg ttttttttggt tttttttta   39000 agtgctttgt agagagcaag gtcttgcctc gttccctaac ccaatcctgg gctttgtttc   39060
tttctttgat ctatttctct cttctgttgt tttctttctt tcaggagaca gggtcttgct   39120
ctgtcaccca gactggagta cagtgtcttg atactagctc actgcaaagt caaattcctg   39180
ggctcaaggg atcctcctgc ctcagccacc tgaggagctg gaactgcagg cctgcgacac   39240
tgcacccagc taatttttttt ttcataaata ttatgctttt gtacccagct ttttttttt   39300 ttttttttta actgcagcct tgacctccca ggcttacatg atcctcccac ctctgcttcc   39360
tgagtagctg tgattacagg tgcatgccac catgcccagt gaattaaaaa aaaaaaagt   39420 ttgtagatat ggggtcccac tgtactgcct aggctggtct taaactcctg agctcaagtg   39480
attctcccac ctcagcctcc taaagtgctg agattcagg cataagcccc tggtgcctgg    39540
ccccagctga attttttgttc ttgtttcttc ataaatattc tgtgtaagta cccagctgat  39600
```

```
tgttttattt tttgtagaga tgggggtctt gatatgttgc tcaagttggt ctcaaactac   39660
tggcctcaag cgatcttcct gcctcagcct cccaaagggc tgggattcca agcatgagcc   39720
accacacctg ccacctcttc tgttattttc tctccatctg gcattctctg actctttcat   39780
ctctaccatg atttgggctt tctcctctcc cttctcttat ttcttcccat tctcctatcc   39840
ccatatcctc cctgctaact cctgataccc acagggcccc tcaatcccat tttagtcagc   39900
ttaagtaaca atagctacta aaacaaaacc cctaagaata tggggtctta acacaacaga   39960
cttgtatttc tcactcatgt aaagtccagt tggcatgggg ggtaaggaag ggtccctctg   40020
ctccatgtag tctctcaggg atccaagcac cttccatcct gtggctctgc aatccttagg   40080
atcttctgta gttctctgca ggattcattc attctagatg gaaataagat tgtgcatggg   40140 ttgttttat gggcatagat agcaatctgt tcagccacct ggccacacct aattgaaaga   40200
ggagctgaga aaggtagtct cactgtgagt ctaggaagaa aagtaaatgg atttgctgaa   40260
ttgctcattc atctttgcca cttcctcctt gatccttcag tttctccacc actgcctcag   40320
ctcccaagac aatgctggac tccctcccac atcaccccac tgaccaagct cctccttccc   40380
cctcaggtct cacactctga ggatgactgt ctagctttca aagttcacca atactttaat   40440
gtagagctta tccagcctgg agcagtcaag gtctacgcct attacaacct gggtgagcag   40500
ccaacctagg gcctggggtc tgatggttcc aggggcctga gagtcccagg tatatatgaa   40560
ttgtggggat ctgagaatga aggtctaagg agtccaggga tttgagcatt cgtagtatga   40620
aggtcccacg ggtctgaggg tcccaaggat ctatgagttg aggttctgag gttctgaggg   40680
gatctgagaa tgatggtcta agcaggccag ggatttcagg attagtaatc tgaaggtccc   40740
agggtctgag agtcccaagg atctatgagt tggttctagg gatctgagac ttggggtct   40800 gatgggttca ggggtctcag ggtcttagga atatgtgagt tgcaggggt tctgaaaata   40860 agggtctaag gattctagat atatgagggt tggaggcctg cgtgtcccag gaatctgatga  40920 atttggggtc tgagggtccc aggcttctgt gagttgagag tctaagagac tcaagggtct   40980
gagaatccca aagatcagaa agtagagggg gtcttgggt ctgagggatc tgagggttg   41040 aagacctagc atctccaggt ctgaagactg agaactgggg atctgggcct cccaggcatg   41100
gtctttggag ggaggccctt atcctctcat cttcacatca catctgcccg cagaggaaag   41160
ctgtacccgg ttctaccatc cggaaaagga ggatggaaag ctgaacaagc tctgccgtga   41220
tgaactgtgc cgctgtgctg agggtgagtt ccctggagcc gggaacaggt gggtctgagc   41280
aagccacact tacccaggtc atctatccca tggtcaggga cccccagacc catacccagg   41340
ggataccaag gggggtaggc tcccagggct ggccacaccc atgggcagta ggccccagat   41400
aaggagtggg acttagaccc tgtctccacc ccaccctgca gagaattgct tcatacaaaa   41460
gtcggatgac aagtcaccc tggaagaacg gctggacaag gcctgtgagc caggagtgga   41520
ctatggtgag tgggtgatgg gtgggggtca cgcatgttta gctgtgtgtg tccaattgtg   41580
tggtgggtgg taggtgtggt tgtcatggtg tggcttcagg ctgtgggtgt gggtgactgt   41640
ggtgtgtgtg agagcatgta ttgtgagggg ccatgattgt gtgggaacc atgactgtga   41700 gtggcctagg tatgctcatg tgagaaaagg tagatgtggt tgtatgcatc attgcgtggg   41760
tggctgtgag gttgtagttg tgtgtggctg tggttgtgtg aggctgtgtg gttgtagatg   41820
gcagtgagtg tgaggtcctg aagttacgta tatgactgta gttttccgtg gctatggttg   41880
tgtgcatggc catgagcta cagtattttg tgcatatgag tcactctcat tgcatagtat   41940
gaatagtatg ttactagaca ttgtgggtgg ctgtgacctc tgtgcatgcc tatgagcacg   42000
```

```
actgtgtgtg gatggtgaca tgggaccctc tatggttgtg tgtgtaatga ggggtgggcc    42060
atagtgtgac tggctgtgat tctgcaactt tctgcttggg agagagagcc acatgcccgg    42120
gtgcacttgc aaaccagggt gcccctcatg gtcaacctag cccaccaccc aaactgtctg    42180
cctctccccc acagtgtaca agacccgact ggtcaaggtt cagctgtcca atgactttga    42240
cgagtacatc atggccattg agcagaccat caagtcaggt caggctcagc acgctgcctc    42300
ccgtggctct tccctggctt cctccccacg actcagcttc ttccctctcc cctccactcc    42360
aggctcggat gaggtgcagg ttggacagca gcgcacgttc atcagcccca tcaagtgcag    42420
agaagccctg aagctggagg agaagaaaca ctacctcatg tggggtctct cctccgattt    42480
ctggggagag aagcccaagt gagtgctttc cctgcgcgtg cgcgcgaccg cccgactgcc    42540
ccgcccatgc cacgcccaca ccattgtcac gcccctgcgc cacgcccaca ccacgcccct    42600
tcctgacctg ccattcttcc ctccagcctc agctacatca tcgggaagga cacttgggtg    42660
gagcactggc ccgaggagga cgaatgccaa gacgaagaga accagaaaca atgccaggac    42720
ctcggcgcct tcaccgagag catggttgtc tttgggtgcc ccaactgacc acacccccat    42780
tcc                                                                 42783
```